(12) United States Patent
Nishiyama et al.

(10) Patent No.: US 8,467,048 B2
(45) Date of Patent: Jun. 18, 2013

(54) PATTERN DEFECT INSPECTION APPARATUS AND METHOD

(75) Inventors: Hidetoshi Nishiyama, Hitachinaka (JP); Kei Shimura, Mito (JP); Sachio Uto, Yokohama (JP); Minori Noguchi, Joso (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/535,955

(22) Filed: Jun. 28, 2012

(65) Prior Publication Data

US 2012/0268734 A1    Oct. 25, 2012

Related U.S. Application Data

(63) Continuation of application No. 12/781,682, filed on May 17, 2010, now Pat. No. 8,233,145, which is a continuation of application No. 12/113,781, filed on May 1, 2008, now Pat. No. 7,746,453.

(30) Foreign Application Priority Data

May 2, 2007    (JP) ................... 2007-121741

(51) Int. Cl.
    *G01N 21/00*    (2006.01)
(52) U.S. Cl.
    USPC ...................................... 356/237.5
(58) Field of Classification Search
    USPC .......................... 356/72–73, 237.5
    See application file for complete search history.

(56) References Cited

U.S. PATENT DOCUMENTS

| 5,046,847 | A | | 9/1991 | Nakata et al. |
| 5,798,829 | A | | 8/1998 | Vaez-Iravani |
| 5,917,602 | A | * | 6/1999 | Bonewitz et al. ............ 356/614 |
| 6,175,645 | B1 | * | 1/2001 | Elyasaf et al. ............... 382/147 |
| 6,552,783 | B1 | | 4/2003 | Schmidt et al. |
| 7,037,735 | B2 | | 5/2006 | Noguchi et al. |
| 7,463,350 | B2 | | 12/2008 | Nishiyama et al. |
| 7,505,125 | B2 | | 3/2009 | Andrews et al. |
| 2001/0048522 | A1 | | 12/2001 | Yonezawa |

(Continued)

FOREIGN PATENT DOCUMENTS

| JP | 61-212708 A | 9/1986 |
| JP | 62-89336 A | 4/1987 |

(Continued)

OTHER PUBLICATIONS

Japanese Office Action in Japanese App. No. 2007-121741 (and partial English translation).

*Primary Examiner* — Tarifur Chowdhury
*Assistant Examiner* — Abdullahi Nur
(74) *Attorney, Agent, or Firm* — Miles & Stockbridge P.C.

(57) ABSTRACT

A pattern defect inspection apparatus capable of detecting minute defects on a sample with high sensitivity without generating speckle noise in signals is realized. Substantially the same region on a surface of a wafer is detected by using two detectors at mutually different timings. Output signals from the two detectors are summed and averaged to eliminate noise. Since a large number of rays of illumination light are not simultaneously irradiated to the same region on the wafer, a pattern defect inspection apparatus capable of suppressing noise resulting from interference of a large number of rays, eliminating noise owing to other causes and detecting with high sensitivity minute defects on the sample without the occurrence of speckle noise in the signal can be accomplished.

15 Claims, 16 Drawing Sheets

U.S. PATENT DOCUMENTS

| | | |
|---|---|---|
| 2006/0124874 A1 | 6/2006 | Uto et al. |
| 2007/0024998 A1 | 2/2007 | Bills et al. |
| 2007/0285658 A1 | 12/2007 | Claps et al. |

FOREIGN PATENT DOCUMENTS

| | | |
|---|---|---|
| JP | 1-117024 A | 5/1989 |
| JP | H-1-117024 | 8/1989 |
| JP | 4-152545 A | 5/1992 |
| JP | 5-218163 A | 8/1993 |
| JP | 11-258157 A | 9/1999 |
| JP | 2000-105203 | 4/2000 |
| JP | 2000-506275 | 5/2000 |
| JP | 2005-156516 | 6/2005 |

* cited by examiner

ILLUMINATION FROM
360° DIRECTION

↑ INCIDENT LIGHT

PATTERN DEFECT INSPECTION APPARATUS AND METHOD

CROSS-REFERENCE TO RELATED APPLICATIONS

This application is a continuation of application Ser. No. 12/781,682 filed May 17, 2010 now U.S. Pat. No. 8,233,145, which is a continuation of application Ser. No. 12/113,781 filed May 1, 2008 now U.S. Pat. No. 7,746,453. The present application also claims priority from Japanese patent No. 2007-121741 filed on May 2, 2007, the contents of which are hereby incorporated by reference into this application.

BACKGROUND OF THE INVENTION

1. Field of the Invention

This invention relates to a pattern defect inspection apparatus for detecting defects and foreign matters of a circuit pattern on a sample.

2. Description of the Related Art

Foreign matters and defects (short-circuit, wire breakage, etc) on a semiconductor wafer, if any, will result in insulation defects and short-circuits of wires and capacitors and film breakage of gate oxide films and eventually, in the defects of semiconductor devices in semiconductor production processes.

Structures of semiconductor devices have got more and more diversified and complicated in recent years. Semiconductor devices are classified into memory products that are constituted mainly of repetition patterns and logic products that are constituted mainly of non-repetition patterns, for example. Since product life of the semiconductor device products is relatively short, the production yield must be improved within a short period. It has thus become more important to reliably find out so-called "target defects" that must be managed during fabrication of the semiconductor devices.

The "target defect" includes voids and scratches in a CMP process in addition to foreign matters and pattern defects in a production process of each of film formation, etching and photolithography. The target defect includes further short-circuit and bridge in gate wiring and metal wiring portions such as aluminum and non-conduction and non-opening of contact apertures that connect wires.

SEM (Scanning Electron Microscope) inspection technology and optical inspection technology are generally known as technology for detecting the target defects on the semiconductor wafer described above. The optical inspection technology is divided into bright visual field inspection technology and dark visual field inspection technology. The bright visual field inspection technology illuminates a wafer through an objective lens and condenses reflected and diffracted rays of light by a condenser lens. The rays of light so diffracted are subjected to photoelectric conversion by detectors and defects are detected by signal processing. On the other hand, the dark visual field inspection technology illuminates a wafer from outside NA (Numerical Aperture) of an objective lens and condenses scattered rays of light by an objective lens. The rays of light so condensed are subjected to signal processing to detect defects in the same way as in the bright visual field inspection technology.

As one of the optical type dark visual field inspection technologies, JP-A-62-89336, for example, describes a detection method that makes it possible to detect foreign matters and defects with high sensitivity and high reliability by irradiating a laser beam onto a wafer, detecting scattered rays of light from the foreign matters and comparing the result with an inspection result of the same kind of wafer inspected immediately before to eliminate false information due to patterns.

As the technology for inspecting the foreign matters described above, JP-A-1-117024, JP-A-4-152545 and JP-A-5-218163, for example, describe a detection method that irradiates coherent light to a wafer, removes the rays of light generated from repetition patterns on the wafer by using a spatial filter, and stresses and detects those foreign matters and defects which do not have repetition characteristics.

A method for detecting minute foreign matters by irradiating light to the same point from multiple directions and detecting scattered rays of light at mutually different angles is known, too (JP-A-11-258157, for example).

SUMMARY OF THE INVENTION

Foundation patterns below the position at which the defect occurs have got diversified in recent years in addition to the reduction of the size of defects themselves (below resolution of an optical system) and their diversification. Consequently, detection of the target defect has become more difficult. Factors that impede the detection of the target defect include grains of metal wires such as aluminum, minute concavo-convexities of a surface called "morphology", non-uniformity of the intensity of interference light due to a very small difference of the film thickness of transparent films (transparent to an illumination wavelength) such as an insulating film, roughness of edge portions of wiring, and so forth.

Development of high NA of an objective lens for inspection and optical super resolution technology has been made as the optical inspection technology. However, because the high NA of the objective lens for inspection has reached a physical limit, an essential approach is to reduce the wavelength of illumination light to UV (Ultra Violet) light and DUV (Deep Ultra Violet) light. To increase light power of the rays of light emitted from a minute target defect, on the other hand, an illumination light source having high luminance is necessary. Therefore, a laser beam source is used in many cases as the illumination light source to acquire illumination light having high luminance in the UV and DUV ranges.

When the laser beam source having such high luminance is used in the prior art technology, however, speckle noise owing to interference of illumination light such as the laser beam source invites the increases of variance of signals detected by detectors and results in noise during signal processing. Consequently, a minute defect cannot be detected highly precisely.

It is therefore an object of the invention to accomplish pattern defect inspection apparatus and method capable of detecting highly precisely minute defects on a sample without generating speckle noise in signals.

To accomplish the object described above, the invention employs the following construction.

In a defect inspection apparatus for detecting a defect on a sample surface, a defect inspection apparatus according to the invention includes an illuminating unit for illuminating a plurality of regions on the sample surface; an image forming unit for forming optical images of the plurality of regions of the sample surface illuminated; a plurality of detecting units for detecting the optical images formed and detecting reflected light from the sample surface; and a defect detecting unit for processing reflected light detected by the plurality of detecting units and detecting a defect on the sample surface.

In a defect inspection apparatus for detecting a defect on a sample surface, a defect inspection apparatus according to the invention includes a multi-direction illuminating unit for illuminating the sample surface from multiple directions among an azimuth of 360 degrees of the sample surface; an imaging forming unit for forming an optical image of the sample surface illuminated by the multi-direction illuminating unit; a plurality of detecting units for detecting the optical image formed by the imaging unit and detecting reflected light from the sample surface; and a defect detecting unit for processing reflected light detected by the detecting units and detecting a defect on the sample surface.

It is preferred in the defect inspection apparatus described above that substantially the same region on the sample surface is illuminated at mutually different timings, mutually different detectors detect reflected light from the same region at mutually different timings and the defect of the same region is detected on the basis of detection signals from the mutually different detectors.

The invention can accomplish pattern defect inspection apparatus and method capable of detecting highly precisely minute defects on a sample without generating speckle noise in signals.

DESCRIPTION OF THE EMBODIMENTS

Preferred embodiments of the invention will be hereinafter explained in detail with reference to the accompanying drawings.

First Embodiment

Figure 1:
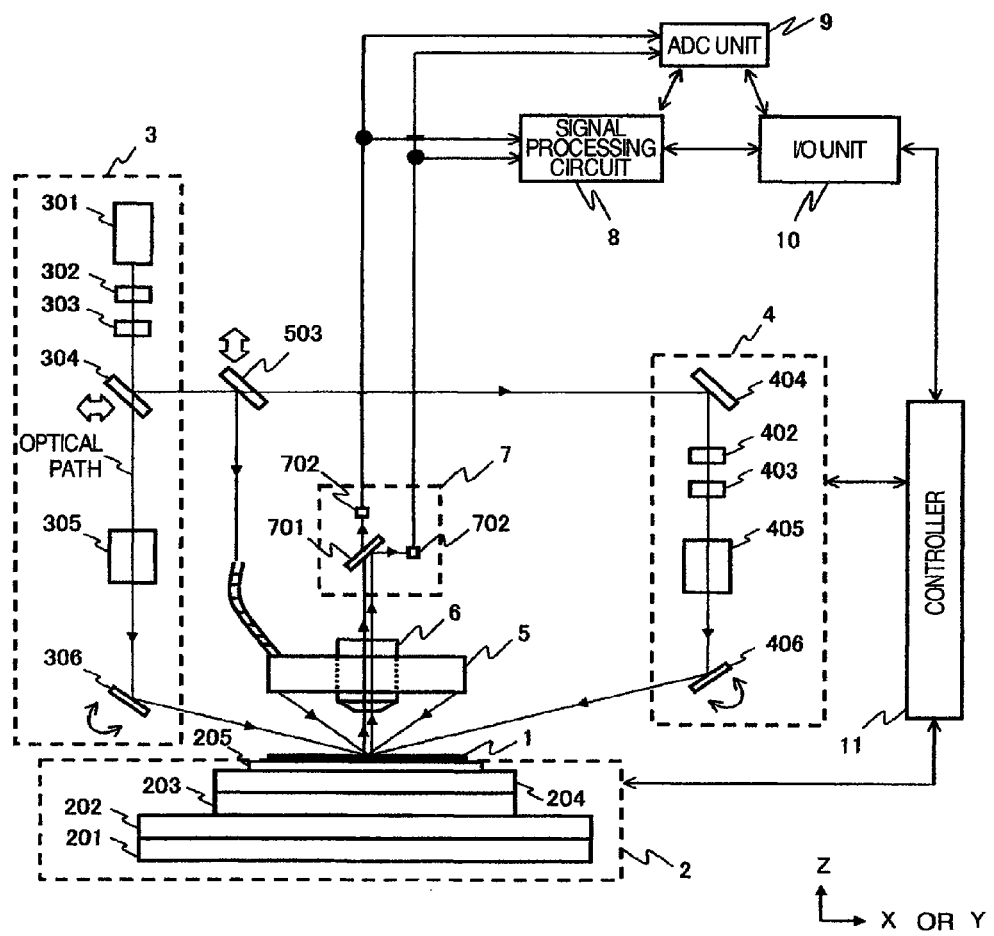
FIG. 1 is a schematic structural view of a pattern defect inspection apparatus according to a first embodiment of the present invention.

FIG. 1 is a schematic structural view of a pattern defect inspection apparatus according to the first embodiment of the invention. The invention will be hereinafter explained about the case where it is applied to the inspection of a semiconductor wafer by way of example.

Referring to FIG. 1, the pattern defect inspection apparatus includes a conveying system 2 for supporting and moving a wafer 1 as an inspection object, illuminating units 3 and 4, a multi-direction illuminating unit 5, an objective lens 6, a multi-region detecting unit 7, a signal processing circuit 8, an ADC (Automatic Defect Classification) unit 9, an input/output unit 10, a controller 11 for each unit and relay lenses and mirrors that are not shown in the drawing. Incidentally, arrows (part of which is not shown) extending from the controller 11 to each unit represents that control signals, etc, are mutually communicated.

Next, the operation will be explained. Beams of illumination light emitted from the illuminating units 3 and 4 or from the multi-direction illuminating unit 5 are irradiated to the wafer 1. The beams scattered by a circuit pattern and defects on the wafer are condensed by the objective lens 6, are subjected to photoelectric conversion by the multi-region detecting unit 7 and are converted to an image signal. This image signal is transmitted to the signal processing circuit 8 and the ADC unit 9. Defect detection processing is executed in the signal processing circuit 8 and defects on the wafer 1 are detected.

The detection result is transmitted to the ADC unit 9 and to the output unit 10. On the other hand, the signal sent to the ADC unit 9 is subjected to defect classification processing and the processing result is sent to the input/output unit 10. The operation described above is carried out while the wafer 1 is being moved by the conveying system 2 and the entire surface of the wafer 1 is inspected.

The input/output unit 10 has an interface function of receiving input information from the user and outputting the information and can transmit and receive control signals to and from the controller 11.

The detail of each unit will be explained.

To begin with, the detail of the conveying system 2 will be explained. The conveying system 2 includes an X-axis stage 201, a Y-axis stage 202, a Z-axis stage 203, a theta-axis stage 204 and a wafer chuck 205. The X-axis stage 102 can travel at a constant speed and the Y-axis stage can move step-wise. All the positions of the wafer 1 can be moved to the center of the objective lens 6 by using the X-axis stage 201 and the Y-axis stage 202.

The Z-axis stage 203 has the functions of moving up and down the wafer chuck 5 and moving the wafer 1 to the focal point of the objective lens 6 on the article side on the basis of a signal from an automatic focusing mechanism that is not shown in the drawing. The -axis stage 204 has the turning function of turning the wafer chuck 205 and bringing the moving direction of both X-axis stage 201 and Y-axis stage 202 into alignment with the turning direction of the wafer chuck 205. The wafer chuck 205 has the function of fixing the wafer 1 by adsorbing it by using vacuum or the like.

The illuminating units 3 and 4 conduct shaping of illumination light to irradiate the wafer 1. The illuminating unit 3 and the illuminating unit 4 can illuminate mutually different positions on the wafer 1. These illuminating units 3 and 4 include an illumination light source 301, light power polarization adjusting units 302 and 402, coherency reducing units 303 and 404, light path switching units 304 and 404, condensation optical systems 305 and 405 and oblique illumination mirrors 306 and 406.

Figure 2:
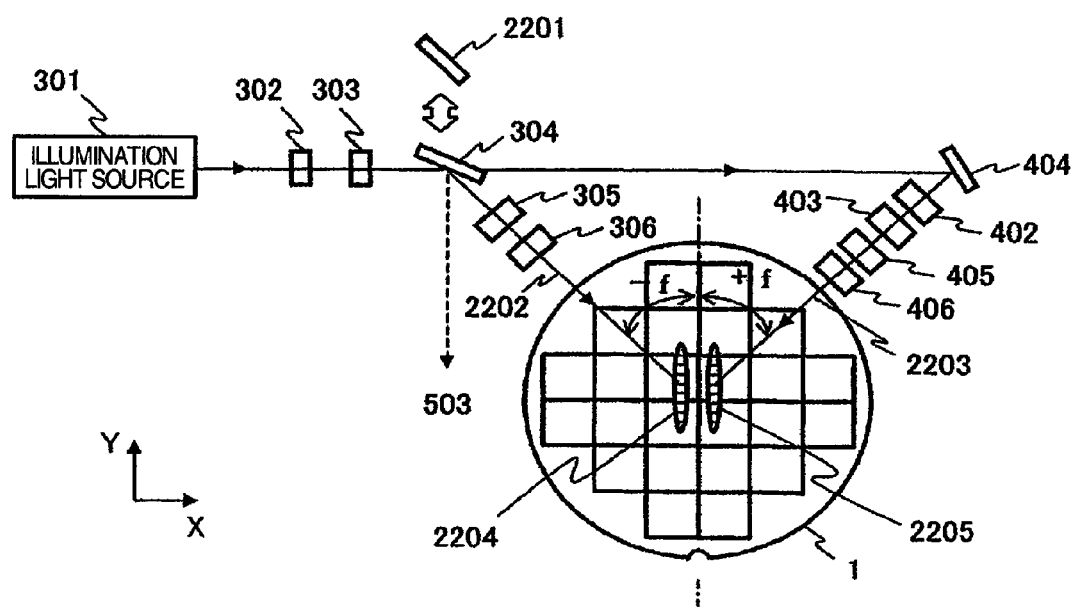
FIG. 2 shows a detailed construction of an illuminating unit shown in FIG. 1.

FIG. 2 shows a detailed construction of the illuminating units 3 and 4. The illumination light source 301 is a laser light source or a lamp light source. Because the laser light source can shape illumination light having high luminance, it can increase light power of scattered light from the defect and is effective for high speed inspection. Because the lamp light source has a low interference property, on the other hand, it has the advantage that a speckle noise reducing effect is great. The wavelength band of the laser light source may be those of visible light, ultraviolet light, deep ultraviolet light, vacuum ultraviolet light, extreme ultraviolet light, and so forth. The oscillation form of laser may be continuous oscillation or pulse oscillation. The wavelength is preferably about 500 nm or below. For example, light sources of 532 nm, 355 nm, 266 nm, 248 nm, 200 nm, 193 nm, 157 nm and 13 nm can be employed.

It is possible to use, as the laser light source, those which execute wavelength conversion of solid YAG laser (wavelength: 1,024 nm) by a non-linear optical crystal and generate second harmonic (SHG), third harmonic (THG) and fourth harmonic (FHG) of the fundamental wave, excimer laser, ion laser, and so forth. It is also possible to use a laser light source of the type which causes resonance of two kinds of light having mutually different wavelengths and oscillates light of another wavelength. This is the method that generates sum frequency resonance of the SHG wave of Ar laser light having a wavelength of 488 nm and YAG laser light having a wavelength of 1,064 nm, for example, and outputs laser having a wavelength of 199 nm. The form of the pulse oscillation laser may be low frequency pulse oscillation laser having an oscillation frequency of several Hz or quasi-continuous wave oscillation pulse laser having an oscillation frequency of dozens to hundreds of Hz. Furthermore, the pulse oscillation method may be either of a Q-switch type or of a mode lock type.

The advantages of the respective light sources are as follows.

First, the light source having a short wavelength can improve resolution of the optical system and a high sensitivity inspection can be expected. Solid laser such as YAG does not call for a large scale installation. Therefore, the scale of the apparatus can be reduced and the cost can be decreased. When pulse oscillation laser having a high frequency is used, the laser can be handled similarly to continuous oscillation laser of a high output. Therefore, economical optical components having low transmission factors and low reflection factors can be used and an economical apparatus can be materialized. Because the coherence distance is short in the case of laser having a small pulse width, coherency can be easily reduced time-wise by adding a plurality of light having varied optical lengths of illumination light.

On the other hand, light sources emitting rays of light in the wavelength range approximate to that of the laser light source can be used as the lamp light source. It is possible to use, for example, a Xe lamp, a Hg—Xe lamp, a Hg lamp, a high pressure Hg lamp, a super-high pressure Hg lamp, an Electron Beam-Gas-Emission-Lamp (output wavelength: 351 nm, 248 nm, 193 nm, 172 nm, 157 nm, 147 nm, 126 nm and 121 nm, for example), and the lamp source is required only to output a desired wavelength. As a selection method of lamps, a lamp having a high output of a desired wavelength may well be selected and an arc length of the lamp is preferably short. For, the formation of illumination light becomes easy.

The light power polarization adjusting unit 302 adjusts illumination light power and the polarization direction of illumination light for the rays of light emitted from the illumination light source 301. An attenuator including an ND (Neutral Density) filter, a ½ wavelength plate and a PBS (Polarized Beam Splitter) is used to adjust light power. A ½ wavelength plate or a ¼ wavelength plate is used to adjust the polarization direction. After light power and the polarization direction are adjusted, coherency of the ray of light is reduced by the coherency reducing unit 303 and the ray is branched by the half mirror in the optical path switching unit 304 to an illumination optical path 2202 and an optical path switching unit 404 or is reflected by a mirror 2201 to a mirror 503.

Here, the coherency reducing unit 303 can use a diffusion plate, for example, but other members can be also used as long as they have the function of deviating at random the phase of light. Furthermore, a mechanism having the function of changing time-wise the position at which illumination light passes may be added.

The ray of light reflected by the half mirror in the optical path switching unit 304 to the illumination optical path 2202 is condensed by the condensation optical system 305 and is irradiated by the oblique illumination mirror 306 to an illumination region 2204. On the other hand, the ray of light passing through the half mirror is reflected by the mirror of the optical path switching unit 404 and travels on an optical path 2203. In this optical path 2203, illumination light power and the polarization direction of the ray of light are adjusted. Coherency is reduced by the coherency reducing unit 403 and the ray of light is condensed in the condensation optical system 405. The ray of light is then irradiated by the oblique illumination mirror 406 to the illumination region 2205 of the wafer 1. In the first embodiment of the present invention, the irradiation direction of the illumination region 2204 is a direction having an angle –f relative to the Y direction of the wafer 1 and the irradiation direction of the illumination region 2205 is a direction having an angle +f relative to the Y direction.

Figure 3:
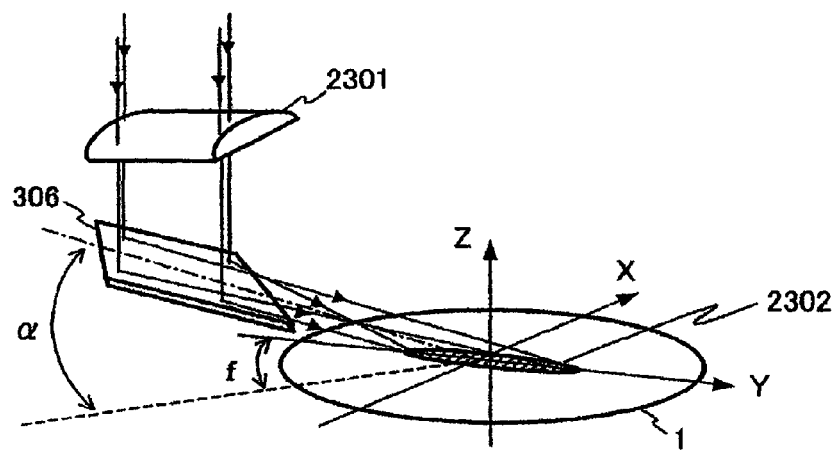
FIG. 3 shows in detail a condensing portion of an illumination light shown in FIG. 1.

FIG. 3 shows the detail of the condensation portion of illumination light. In FIG. 3, the condensation optical system 305 has a cylindrical lens 2301 and a relay lens which is not shown in the drawing. The ray of light condensed by the cylindrical lens 2301 is condensed by the oblique illumination mirror 306 on the illumination region 2302 on the wafer 1. At this time, illumination light forms an elongated linear illumination region in the Y direction. The oblique illumination mirror 306 can rotate with respect to the optical axis and can change the illumination angle α when its reflection surface is rotated. When the illumination angle α is changed, however, the oblique illumination mirror 306 can move in the Z direction lest the position of the illumination region 2302 is changed. Incidentally, the condensation optical system 405 and the oblique illumination mirror 406 have the same construction as those of the condensation optical system 305 and the oblique illumination mirror 306, respectively.

Here, the illumination angle α may be decided in accordance with the kind of defects occurring in the inspection object. When detection is mainly directed to foreign matters on the surface of the wafer 1, the illumination angle α is preferably parallel to the wafer surface 1 and is from about 1 to about 5 degrees. When the illumination angle is nearly parallel to the wafer surface 1, an SNR (Signal to Noise Ratio) of the foreign matters on the wafer surface 1 can be improved. When detection is mainly directed to a pattern defect or a foreign matter having a small height, illumination is preferably made from a high angle. When the angle is too high, however, optical power of reflection and diffraction from a circuit pattern as a base becomes great and the SNR drops. Therefore, the illumination angle α is preferably from 45 to about 55 degrees.

To uniformly detect the foreign matter and the pattern defect on the wafer surface 1 described above, an intermediate angle of the angles described above is preferable and the illumination angle α is preferably set to about 20 degrees. Furthermore, when a correlation exists between the process of the inspection object and the kind of the defect to be detected such as when it is known in advance that the defects to be mainly detected in the wiring process are foreign matters having small height, decision may be made in advance to the effect that "illumination is made from a high angle in the wiring process". The illumination angle of the illuminating unit 3 may be the same as or different from that of the illuminating unit 4. These units are preferably used at mutually different angles when an optimal angle exists depending on the kind of the defects as described above.

Next, the multi-direction illuminating unit 5 will be described in detail.

Figure 4A:
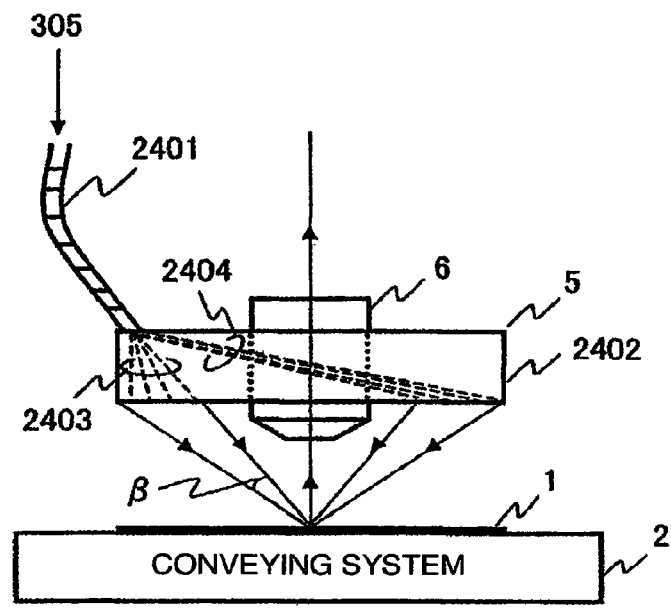
FIGS. 4A and 4B show an example of a multi-direction illuminating unit.
Figure 4B:
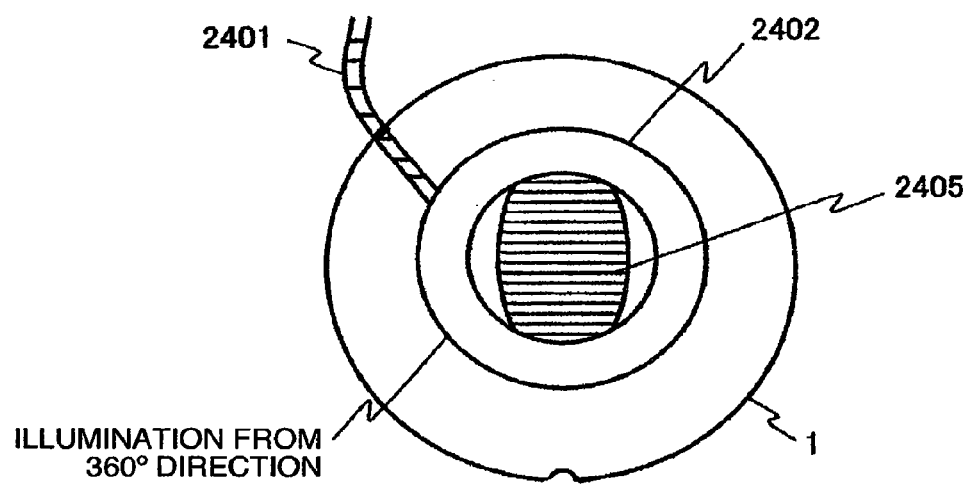

The multi-direction illuminating unit 5 has the functions of conducting illumination from outside the range of NA of the objective lens 6 and from multiple directions around the objective lens 6. In other words, this illuminating unit 5 has the function of conducting illumination from multiple directions in the azimuth of 360 degrees of the surface of the wafer 1 (sample surface). FIG. 4 shows an example of the multi-direction illuminating unit 5. FIG. 4A is a side view of the multi-direction illuminating unit and FIG. 4B is its top view.

The multi-direction illuminating unit 5 includes a fiber bundle 2401 for introducing light and a ring-like fiber 2402. The rays of light reflected by the mirror 305 are introduced by the fiber bundle 2401 into the ring-like fiber 2402 and illuminate the visual field 2405 of the objective lens 6 from the direction of 360 degrees around the objective lens 6. Incidentally, illumination light is condensed at an open angle β to the wafer 1.

Here, the distance from an inlet of the fiber bundle 2401 can be changed when light is introduced from the fiber bundle 2401 to the ring-like fiber 2402. In other words, because a luminous flux 2403 is irradiated to the wafer 1 from the position close to the fiber bundle 2401, it moves in a short distance inside the ring-like fiber bundle 2402. On the other hand, because a luminous flux 2403 exists on the opposite side to the luminous flux 2403 while sandwiching the objective lens 6 between them, it moves in a long distance inside the ring-like fiber 2402. In this way, the optical path length of illumination light irradiated to the wafer 1 in each illumination direction can be changed and coherency of light can be reduced time-wise. Furthermore, because illumination is made from multiple directions, scattering direction dependence of the defect and the pattern on the illumination direction can be reduced and stable images can be acquired.

Incidentally, the illuminating unit 3, the illuminating unit 4 and the multi-direction illuminating unit 5 may be used selectively in accordance with the kind of wafers 1. For example, the illuminating unit 3 and the illuminating unit 4 are used to effectively utilize the effect of the later-appearing spatial filter for memory products. For logic products, on the other hand, the multi-direction illuminating unit 5 is employed to effectively reduce the speckle noise. The illuminating unit 3 and the illuminating unit 4 are used for the wafers in the deposition film process and the multi-direction illuminating unit 5 is used for the wafers in the etching process.

Next, the objective lens 6 has the function of condensing the scattered rays of light from the region illuminated by the illuminating units 3 and 4 or by the multi-direction illuminating unit 5. Incidentally, this objective lens 6 must be subjected to aberration correction in the wavelength band of illumination light. However, the construction of the objective lens 6 may be of a refraction type lens or when an illumination light source of a wavelength not transmitting through the lens is used, a reflection type lens constituted by reflecting plates having a radius of curvature may be used, too.

Figure 5A:
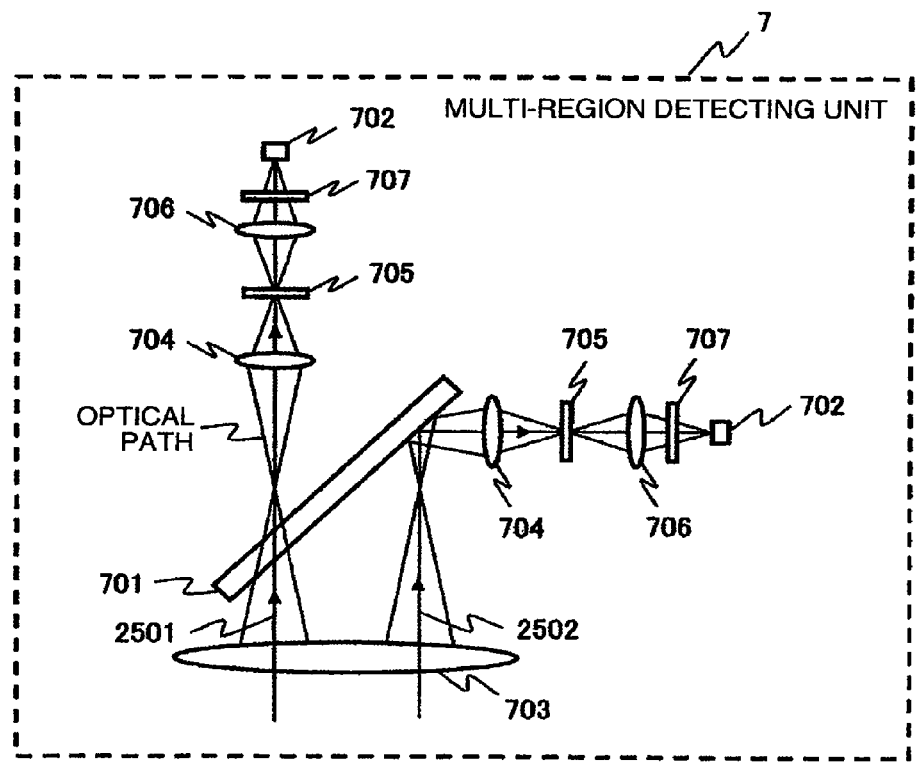
FIGS. 5A and 5B are detailed explanatory views of a multi-region detecting unit.
Figure 5B:
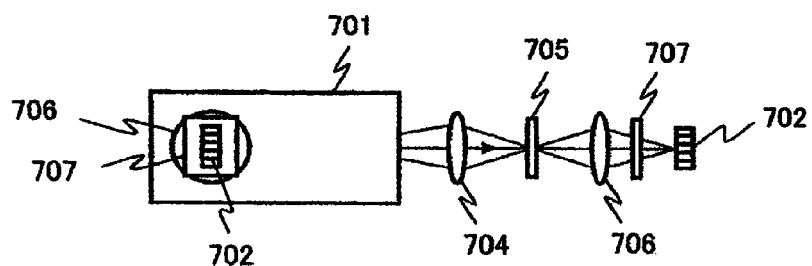

FIG. 5 is a detailed explanatory view of the multi-region detecting unit 7. FIG. 5A is a side view of the multi-region detecting unit 7 and FIG. 5B shows its top. Referring to FIG. 5, the multi-region detecting unit 7 includes a beam splitter 701, a detector 702, relay lens group 703, 704 and 706, a spatial filter 705 and a polarization detecting element 707. The relay lens group 703 and 704 has the function of condensing the rays of light leaving the objective lens 6 and condensing also a Fourier transform image of rays of light scattered by the wafer 1 to the position of the spatial filter 705. The relay lens group 706 has the function of forming an image of the rays of light passing through the spatial filter 705 to the detector 702. Here, an optical path 2501 represents the rays of light scattered by the illumination region 2204 and an optical path 2502 represents the rays of light scattered by the illumination region 2205. In the case of illumination by the multi-direction illuminating unit 5, the rays of light are scattered light at the positions corresponding to the illumination region 2204 and the illumination region 2205.

Here, the spatial filer 705 is used to optically remove information of the circuit pattern on the wafer 1. The Fourier transform image of the circuit pattern on the wafer 1 is formed by condensation patterns at the position corresponding to the wavelength of illumination light, the illumination angle and a repetition pitch of the circuit patterns. The spatial filter 705 shades the rays of light of the condensation pattern. The rays of light of the circuit pattern of the portion corresponding to this condensation pattern can be prevented from reaching the detector 702. Because the condensation pattern of the Fourier transform image changes with the optical condition and with the kind of the circuit pattern, the spatial filter 705 must have the function of being able to change the shading position.

Figure 6A:
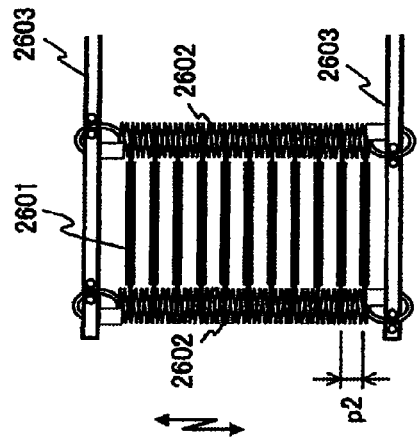
FIGS. 6A and 6B are explanatory views useful for explaining an example of a spatial filter.
Figure 6B:
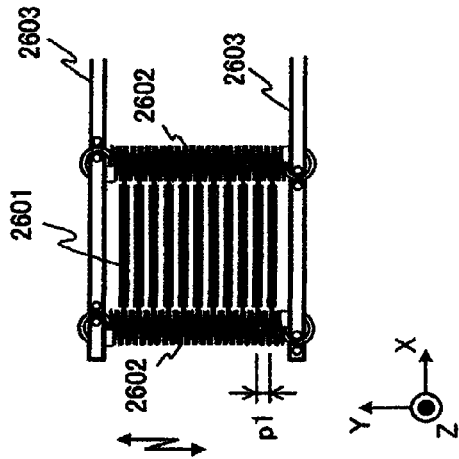

Next, examples of the spatial filter 705 will be explained with reference to FIGS. 6A and 6B and FIGS. 7A and 7B. The example shown in FIGS. 6A and 6B is an example of the spatial filter on a plane (optical axis: Z direction) vertical to the optical axis. The example shown in FIGS. 6A and 6B includes a plurality of shading plates 2601, two springs 2602 and two supporting rods 2603. The shading plate 2601 is formed of a metal sheet but the shading plate is not limited to the metal sheet and other materials can be used as long as they have the shading function.

Both ends of the shading plate 2601 are put on the spring 2602 and both ends of the spring 2602 are disposed on the supporting rods 2603. FIG. 6A shows the condition where a mutual pitch of a plurality of shading plates 2601 (distance between the shading plates) is set to p1. In contrast, FIG. 6B shows the condition where the spring 2602 is stretched as the supporting rod 2603 is moved in the Y direction and the pitch of the shading plate 2601 changes to p2. The optical axis exists in the Z direction.

In the example shown in FIGS. 6A and 6B, therefore, the shading position can be changed in the Y direction by changing the mutual gap of the two supporting rods 2603.

Figure 7A:
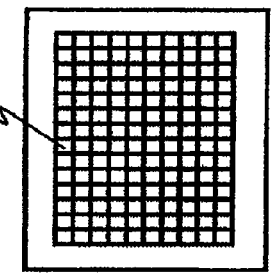
FIGS. 7A and 7B are explanatory views useful for explaining another example of the spatial filter.
Figure 7B:
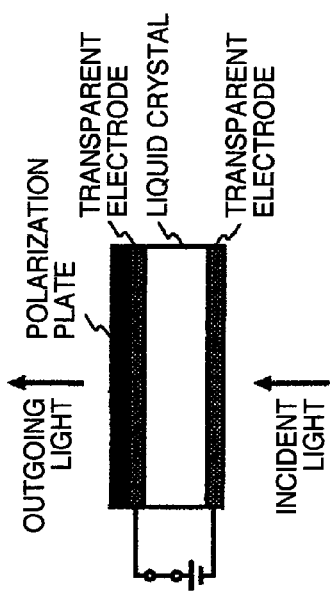

FIG. 7 shows another example of the spatial filter 705 that uses a liquid crystal device. FIG. 7A shows the side surface of the spatial filter 705 and FIG. 7B shows the top. The polarization direction of incident light of each cell is changed by an impressed voltage in the liquid crystal device and a specific polarization component can be removed, that is, shaded, by a polarizing plate on the outgoing side. The advantage brought forth by using the liquid crystal device in the example shown in FIG. 7 is that the shading position can be changed two-dimensionally by the impressing condition of the voltage.

The polarization detecting device shown in FIG. 5 is a polarizing plate. However, it is not always necessary and can be removed from the optical path. The detector 702 has the function of photo-electrically converting incident light. An example of the detector 702 is an image sensor, which may be one-dimensional CCD sensor, a TDI (Time Delay Integration) image sensor or a photo multiplier. Two-dimensional CCD sensors such as a TV camera may be used and a high sensitivity camera such as EB-CCD camera may be used, too. A sensor the speed of which is increased by dividing a detection pixel of the CCD into a plurality of TAP may be used, as well. Furthermore, a surface irradiation type sensor which conducts irradiation from the CCD surface may be used and a back surface irradiation type sensor on the opposite side to the CCD surface can be used. The back surface irradiation type is preferred for wavelengths shorter than ultraviolet light.

As a selection method of the detector 702, a TV camera or a CCD linear sensor is preferably used to constitute an economical inspection apparatus. When weak light is detected with high sensitivity, it is advisable to use a TDI image sensor, a photo multiplier or an EB-CCD camera. The advantage of the TDI image sensor is that the SNR of the detection signal can be improved by adding a plurality of times the detection signal.

Incidentally, when the TDI image sensor is used, the sensor is preferably driven in synchronism with the operation of the conveying system 2. When a high speed operation is necessary, a sensor having a TAP construction is preferably selected. When a dynamic range of the rays of light received by the detector 702 is great, or in other words, when the rays of light inviting saturation of the sensor are incident, a sensor having as an accessorial function the anti-blooming function is preferably used.

Figure 8A:
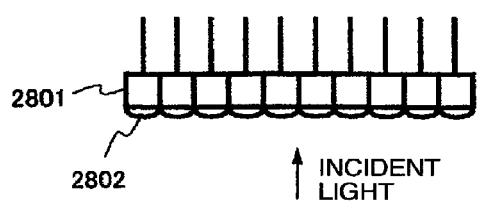
FIGS. 8A and 8B show an example where a photo multiplier is used as a detector.
Figure 8B:
Figure 9:
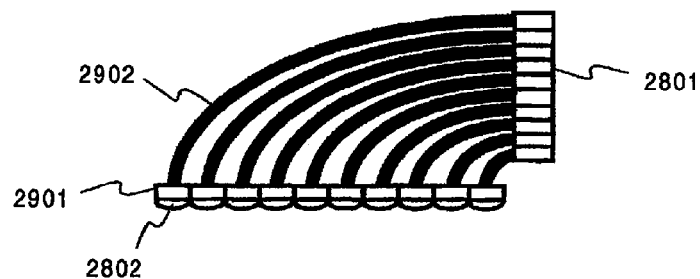
FIG. 9 shows another example where the photo multiplier is used as the detector.

Next, FIGS. 8 and 9 show the construction when a photo multiplier is used for the detector 702. FIG. 8A shows a side surface of the photo multiplier unit and FIG. 8B shows its lower surface. When the photo multiplier is used, it is advisable to use a sensor having a plurality of photo multipliers aligned in a unidimensional direction as shown in FIG. 8. According to this construction, the photo multipliers can be used as the unidimensional sensor having high sensitivity and can conduct high sensitivity inspection. As the construction in this case, a micro-lens 2802 is fitted to the photo multiplier 2801 on the side of incident light as shown in FIG. 8A to condense the rays of incident light to the photo multiplier 2801. The micro-lens 2802 has the function of condensing the rays of light within a range equal to the photo multiplier surface to the photo multiplier. 2801.

It is also possible to employ the construction in which an optical fiber 2902 is fitted through a holder 2901 disposed on the downstream side of the micro-lens 2802 and a photo multiplier 2801 is fitted to the output end of the optical fiber 2902 as shown in FIG. 9. In this case, since the diameter of the optical fiber 2902 is smaller than the diameter of the photo multiplier 2801, the sensor pitch can be decreased in comparison with the example shown in FIG. 8 and a sensor having high resolution can be provided.

Figure 10A:
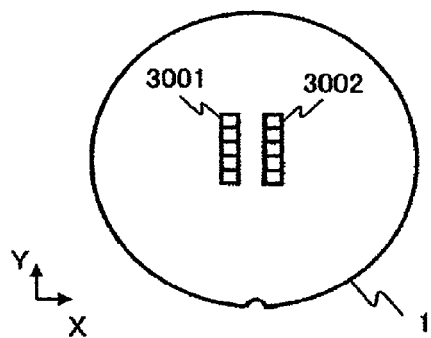
FIGS. 10A and 10B show an example of the arrangement of the detectors.

FIG. 10 shows an example of the arrangement of the detector 702. The drawing shows the state where the detector 702 is projected to the surface of the wafer 1. In the projection images 3001 and 3002 of the detector 702 that are shown in FIG. 10A, the detector 702 is arranged in such a fashion as not to cause a deviation in the Y direction. In the example shown in this drawing, the circuit pattern on the wafer 1 passes through the same pixel f two detectors 702.

Figure 10B:
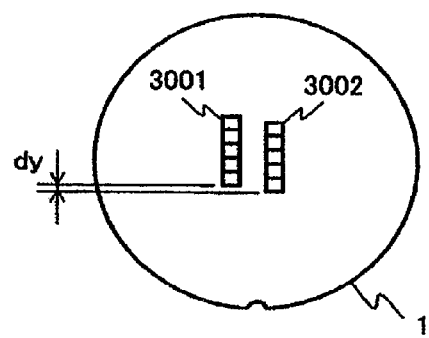

On the other hand, FIG. 10B shows an example of the arrangement where the projection images 3001 and 3002 are deviated by dy. According to the arrangement shown in FIG. 10B, the circuit pattern on the wafer 1 passes through the position deviated by dy in the two detectors 702.

Figure 11:
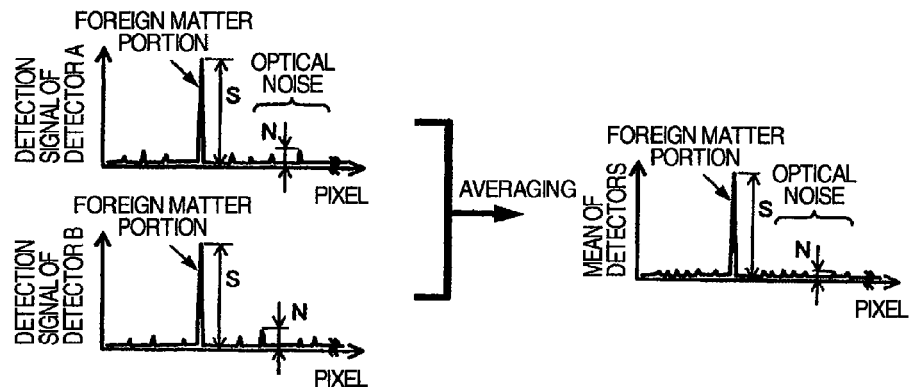
FIG. 11 shows signals when the same foreign matter on a wafer is detected by two detectors.

The effect brought forth by synthesizing the detection signals obtained by the arrangement shown in FIG. 10A will be explained. FIG. 11 shows signals when the same foreign matter on the wafer 1 is detected by two detectors A and B. In comparison with the SNR of the foreign matter by the single detector, the SNR of the foreign matter can be improved by averaging the two detection signals as shown in FIG. 11 for the following reason. Because the optical noise of the background occurs at random timing, the optical noise can be reduced by averaging the two detection signals. However, because the occurrence of the foreign matter signal is not random, the signal drop of the foreign matter signal does not occur. This also holds true of the circuit pattern signal (signal of the pattern the signal reduction of which cannot be made by the spatial filter). In consequence, the SNR of the circuit pattern signal can be improved, the stable signals can be acquired and the defect can be detected at high sensitivity by signal processing that will be later described.

According to the arrangement shown in FIG. 10B, on the other hand, a signal having higher resolution can be obtained than the detection signal acquired by the signal detector by synthesizing the detection signals at deviated positions. In other words, insensitive zones occur among pixels in a detector having a plurality of pixels aligned such as a CCD sensor. When the two detectors are deviated from each other by ½ pixel, the insensitive zone of one of the detectors can be detected by the other detector and can be thus eliminated. Therefore, signals having resolution that is about twice the resolution of the signal detector can be obtained by synthesizing these detection signals.

The example given above represents the case where the detection signals of the detectors A and B are averaged but processing other than averaging processing can be employed, too. For example, a signal having a lower noise level can be employed by adopting the smaller one of the output signals of the detectors A and B.

When the signals of both detectors A and B are compared and their ratio is outside a predetermined range, there is the possibility that either one, or both, of the detectors A and B are in trouble. Therefore, alarm display is made by using suitable alarm means or the result acquired is discarded and output is made with notice to the effect that reliability is low so that re-measurement can be made automatically.

Figure 12:
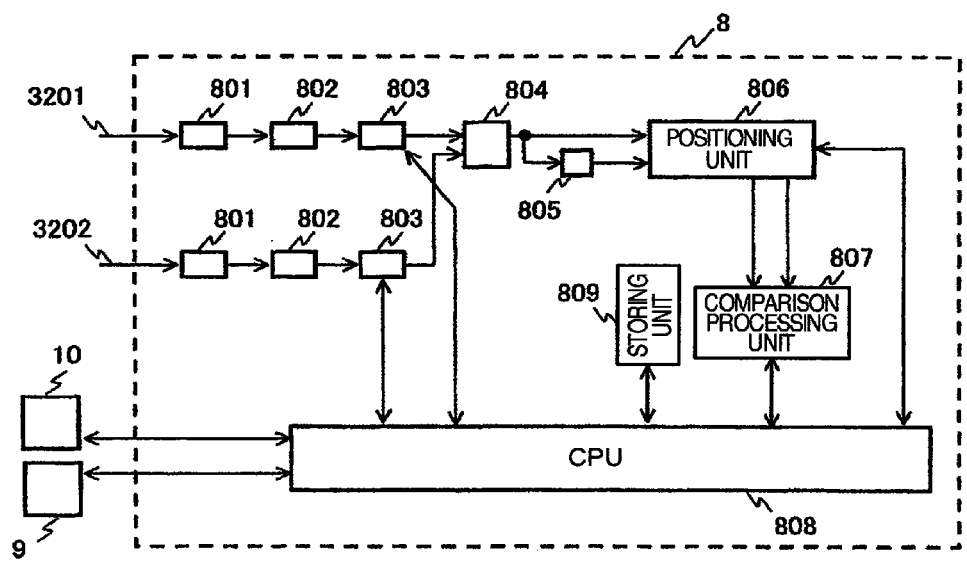
FIG. 12 is an explanatory view useful for explaining a signal processing circuit unit.

Next, the detail of the signal processing circuit 8 will be explained with reference to FIG. 12. Referring to FIG. 12, the signal processing circuit 8 includes a gradation converting unit 801, a filter 802, a delay memory 803, a signal synthesizing unit 804, a delay memory 805, a positioning unit 806, a comparison processing unit 807, a CPU 808 and storing unit 809.

Subsequently, the operation of the signal processing circuit 8 will be explained. First, the detection signals 3201 and 3202 obtained by the detector 702 are subjected to gradation conversion by the gradation converting unit 801 of the signal processing circuit 8. This gradation conversion is analogous to the one described in JP-A-8-320294, for example. The gradation converting unit 801 corrects the signal by linear conversion, logarithmic conversion, exponential conversion, polynomial conversion, and so forth. At this time, the detection signals 3201 and 3202 may be subjected to mutually different conversions. For example, different conversions are carried out to normalize the output signal of the gradation converting unit 801 when the photoelectric conversion characteristics of the two detectors 702 are mutually different.

Next, the filter 802 is the one that removes noise unique to the optical system from the signal subjected to the gradation conversion by the gradation converting unit 801 and is an averaging filter, or the like. The delay memory 803 is a signal delaying unit for delaying the signal used for the signal synthesizing processing executed in a later stage and has the function of storing the signals outputted from the filter 802 in a repetition unit constituting the wafer 1, that is, a unit of one cell or a plurality of cells or one die or a plurality of dies.

Here, the cell is a repetition unit of the circuit pattern inside the die. Incidentally, the filter 802 may be applied after passing through the delay memory 803.

Next, the signal synthesizing unit 804 has the function of synthesizing the signal obtained by processing the detection signal 3201 and the signal obtained by processing the detection signal 3202. For example, it is the processing for averaging the signals corresponding to the same position on the wafer 1. The random noise can be reduced and the stable signal can be obtained by averaging the output signals of the two detectors A and B. The delay memory 805 is a signal storing unit for delaying the signal used for positioning processing that is executed in a later stage.

The positioning unit 806 has the function of detecting the positioning error between the signal outputted from the signal synthesizing unit 804 (detection signal obtained from the wafer 1) and the delay signal obtained from the delay memory 805 (reference signal as reference) and conducting positioning in a pixel unit or below the pixel unit. In other words, the positioning unit 806 conducts positioning of the signal to clarify from which position in the detected region the signal exists in substantially the same region on the wafer 1 for the signals detected by the two detectors with timing deviated from each other.

The comparison processing unit 807 is the unit for detecting the defect on the basis of the difference of the feature volumes by comparing the detection signals outputted from the positioning unit 806. Layout information of the device on the wafer 1 is inputted in advance from the input/output unit 10 and the CPU 808 generates a defect position and feature volume data in the layout on the wafer 1 and stores them in the storing unit 809. The defect position and the feature volume data are sent to the ADC unit 9 and the input/output unit 10, whenever necessary. Incidentally, the detail of the comparison processing unit 807 may be the same as the one disclosed in JP-A-61-212708 and includes, for example, a difference signal detection circuit of a positioned signal, a circuit for detecting non-coincidence by binarizing the difference signal and a feature volume extraction circuit for calculating an area, a length (projection length) and coordinates from the binarized output.

The ADC (Automatic Defect Classification) unit 9 has the function of classifying the kinds of detected matters from the signals detected by the inspection apparatus according to the first embodiment of the invention. Its operation is as follows.

First, the signal acquired by the detector 702 is transmitted to the signal processing circuit 8 and the ADC unit 9. The signal processing circuit 8 carries out the defect defection processing. When the defect is judged as existing, a defect detection flag and the feature volume processed by the signal processing circuit 8 are transmitted to the ADC unit 9. When receiving the defect detection flag, the ADC unit 9 classifies the kind of the defect from the feature volume of the defect portion on the basis of the signal obtained by the detector 702 and the data transmitted from the signal processing circuit 8. The classification method maps various kinds of feature volumes on poly-dimensional coordinate axes and divides the region by a predetermined threshold value. The defect kind of the data existing in the divided region is set in advance and the kind of defect is decided. The defect kind so decided is transmitted as the classification information to the input/output unit 10 and is displayed as the defect information.

The term "feature volume" described above means the sum of the signal values of the defect portion, the differentiation value of the signal value, the number of pixels, the projection length, the centroid position, the signal values of normal portions compared, and so forth. The feature volumes associated with the position include the distance from the center of the wafer 1, the number of times of repetition of the wafer 1 per die, the position inside the die, and so forth.

Next, the input/output unit 10 will be explained. The input/output unit 10 is an interface unit with users and is also an input/output unit of data and control signals. The input information from the users are the layout information of the wafer 1, the names of processes, condition of the optical system mounted to the defect inspection apparatus according to the first embodiment of the invention, and so forth, for example. The output information for the users includes the map of the defect detection positions, the kind of the defects detected, the images, and so forth.

As explained above, the first embodiment of the invention employs the construction in which substantially the same region of the surface of the wafer 1 is detected at different timings by using two detectors and the noise is eliminated by using the output signals from the two detectors. According to this construction, a large number of rays of illumination light are not irradiated simultaneously to the same region on the wafer. Therefore, the invention can realize a pattern defect inspection apparatus, and a method for the apparatus, that can eliminate noise resulting from other causes without inviting the occurrence of the noise owing to interference of a large number of rays of illumination light and can detect minute defects on the sample with high sensitivity without generating the speckle noise in the signals.

Second Embodiment

Next, the second embodiment of the invention will be explained. In this second embodiment, the construction of the illuminating units 3 and 4 of the defect inspection apparatus is different from the construction in the first embodiment. Since the rest of the constructions are the same, their detailed explanation will be omitted.

Figure 13:
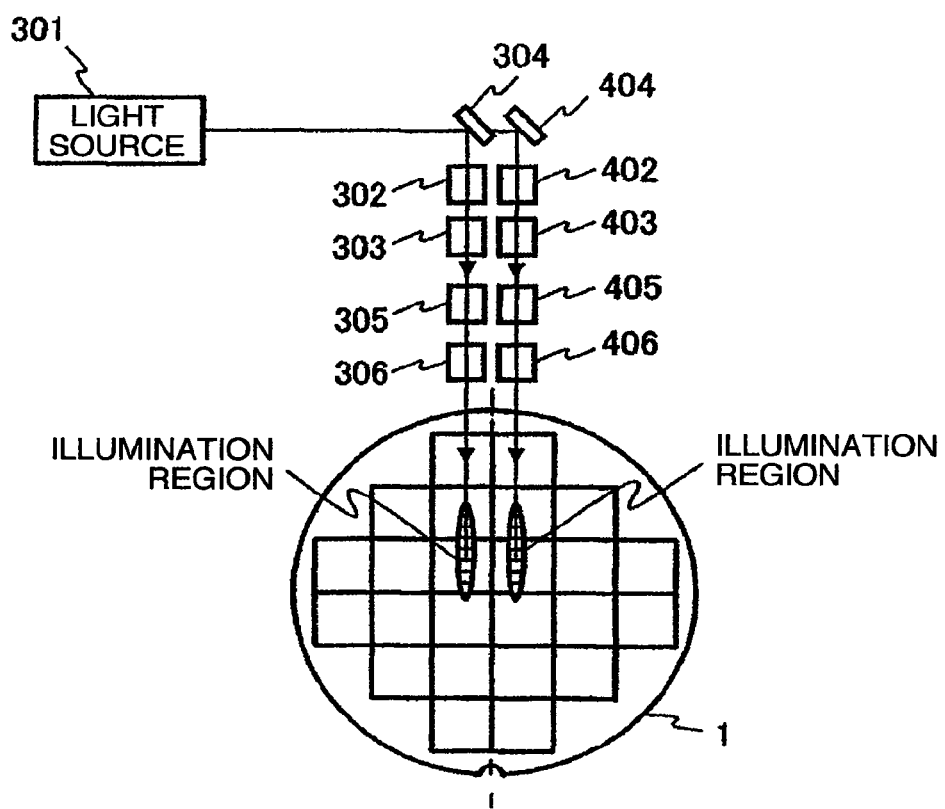
FIG. 13 shows a schematic construction of an illuminating unit according to the second embodiment of the invention.

FIG. 13 shows the construction of the illumination of the second embodiment for illuminating a plurality of regions on the wafer 1. The difference of the example shown in FIG. 13 from that of FIG. 2 resides in that whereas illumination is made from ±f directions with respect to the X or Y direction of the conveying system 2 in the example shown in FIG. 2, it is made from the same direction, that is, from the direction of f=0 in the example shown in FIG. 13.

The advantage of the construction of the illuminating unit shown in FIG. 13 is that the size of the construction of the apparatus can be reduced because the illumination direction and the longitudinal direction of illumination are equal.

In other words, the second embodiment of the invention provides the effect that the apparatus construction of the defect inspection apparatus can be made small in addition to the similar effect of the first embodiment.

Third Embodiment

Next, the third embodiment of the invention will be explained. In the third embodiment, the construction of the illuminating unit 3 of the defect inspection apparatus is different from the construction in the first embodiment. Since the rest of the constructions are the same, their detailed explanation will be omitted.

Figure 14:
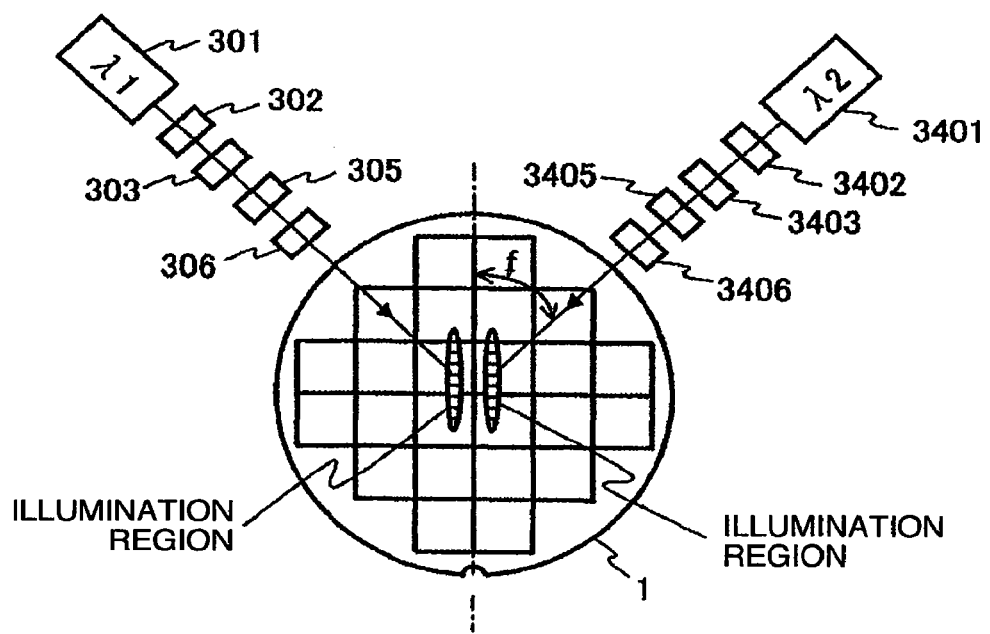
FIG. 14 shows a schematic construction of an illuminating unit according to the third embodiment of the invention.

FIG. 14 shows a schematic construction of the illuminating unit in this third embodiment. The third embodiment uses a plurality of light sources of the illuminating unit. In FIG. 14, an illumination light source 3401 of a wavelength λ2 different from the wavelength λ1 of the illumination light source 301, a light power polarization adjusting unit 3402, a coherency reducing unit 3403, a condensation optical system 3405 and an oblique illumination mirror 3406 are arranged in place of the illuminating unit 4.

The functions of the light power polarization adjusting unit 3402, the coherency reducing unit 3403, the condensation optical system 3405 and the oblique illumination mirror 3406 are equivalent to those of the light power polarization adjusting unit 302, the coherency reducing unit 303, the condensation optical system 305 and the oblique illumination mirror 306, respectively, and the difference resides only in that wavelengths that are subjected to aberration correction are different in the optical system.

The advantage brought forth by illumination with different wavelengths is that influences of thin membrane interference in the transparent film formed on the surface of the wafer 1 can be reduced. In other words, because the change quantity of light power due to the thin membrane interference of the wavelength λ1 and the light power change due to the thin membrane interference of the wavelength λ2 with respect to the film thickness are different, the power volume changes can be averaged and stable signals can be obtained when illumination is made with different wavelengths.

This means that the third embodiment of the invention provides the effect that the power volume changes can be averaged and stable signals can be obtained in addition to the effect similar to that of the first embodiment.

Fourth Embodiment

Next, the fourth embodiment of the invention will be explained with reference to FIGS. 15 to 17. In the fourth embodiment, the construction of a multi-direction illuminating unit is different from the multi-direction illuminating unit 5 in the first embodiment. The rest of the constructions are equivalent to those of the first embodiment.

Figure 15A:
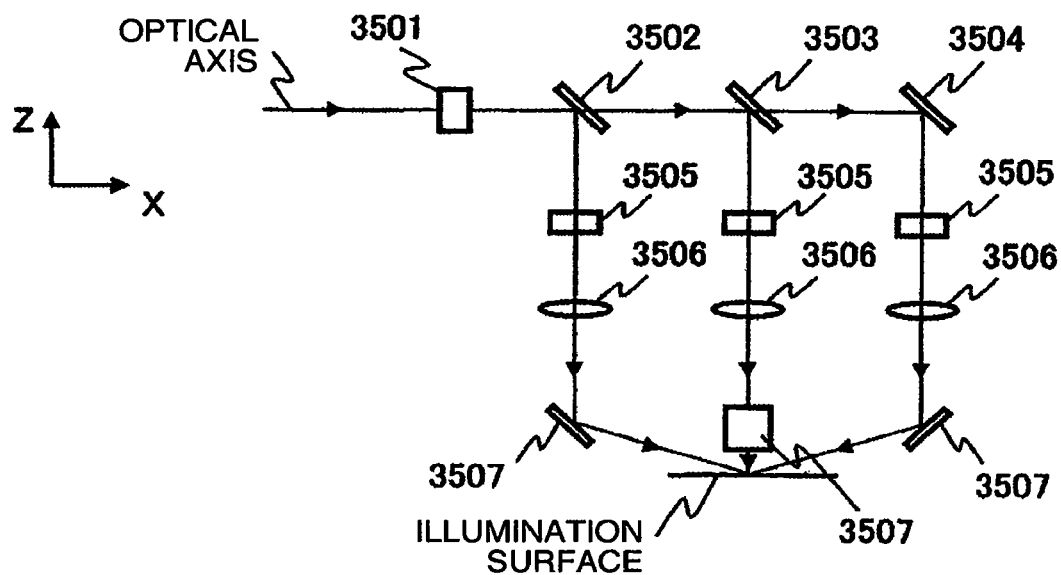
FIGS. 15A and 15B show an example of a multi-direction illuminating unit in the fourth embodiment of the invention.
Figure 15B:
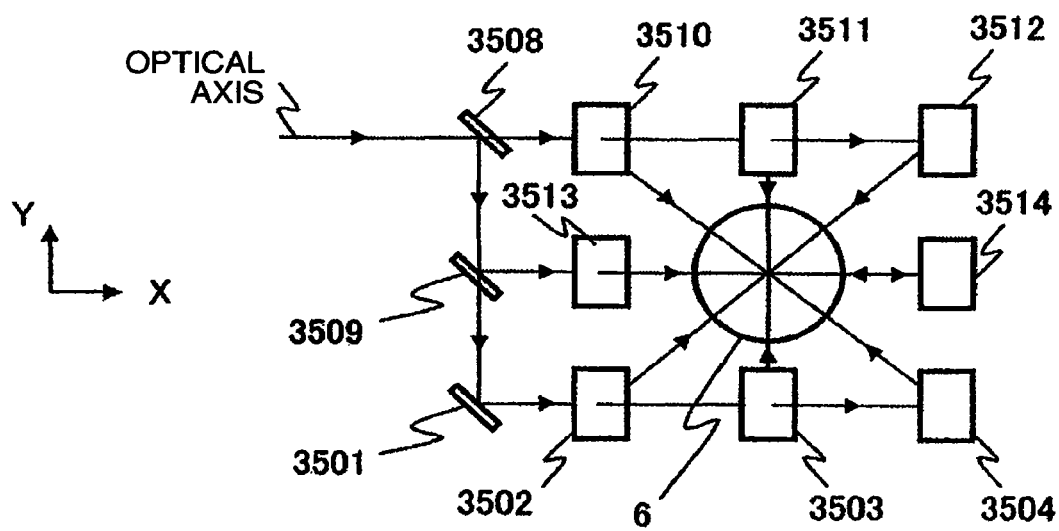

FIG. 15A shows the side of the multi-direction illuminating unit in the fourth embodiment and the illuminating unit includes total reflecting mirrors 3501, 3504, 3507, 3512 and 3514, partial mirrors 3502, 3503, 3508, 3509, 3510, 3511 and 3513, a polarization controlling unit 3505 and a relay lens 3506.

Next, the operation will be explained. The rays of light reflected by the mirror 503 are branched into the rays traveling in the direction of the mirror 3509 and the rays traveling in the direction of the mirror 3510. The rays of light incident into the mirror 3510 are branched into the rays traveling in the direction of the mirror 3511 and the rays traveling in the direction of the polarization controlling unit (Z direction shown in FIG. 15).

Similarly, the rays of light are branched by each partial mirror into two directions and are reflected by each total reflecting mirror into one direction. The rays of light reflected by the mirrors 3402, 3503, 3504, 3510, 3511, 3512, 3513 and 3514 in the Z-axis direction are subjected to polarization adjustment by the polarization controlling unit 3505 and are then condensed by the total reflecting mirror 3507 to the focal plane of the objective lens 6 through the relay lens 3506.

Figure 16:
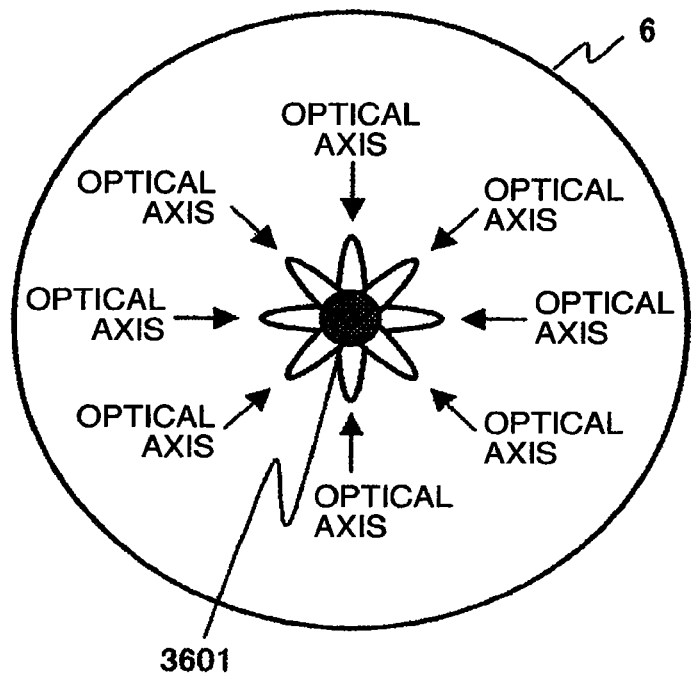
FIG. 16 is an explanatory view useful for explaining light condensation in the fourth embodiment of the invention.

FIG. 16 shows the mode of condensation. In FIG. 16, the rays of condensed light conduct illumination from 8 directions to the visual field of the objective lens 6 so that all illuminations overlap with one another in the illumination region 3601.

Here, the reflection factor of each partial mirror is changed so that the intensity of light incident to the total reflecting mirror 3507 is substantially equal. The polarization controlling unit 3505 is constituted by a ½ wavelength plate and a ¼ wavelength plate. The advantage of this fourth embodiment is that the polarization direction of each illumination irradiated to the wafer 1 can be controlled by the polarization controlling unit 3505.

For example, illumination in total directions can be adjusted to S polarized light, and S polarized and P polarized light can be mixed in accordance with the illumination direction. The polarization direction of illumination light may be decided in accordance with the surface condition of the wafer 1.

Figure 17:
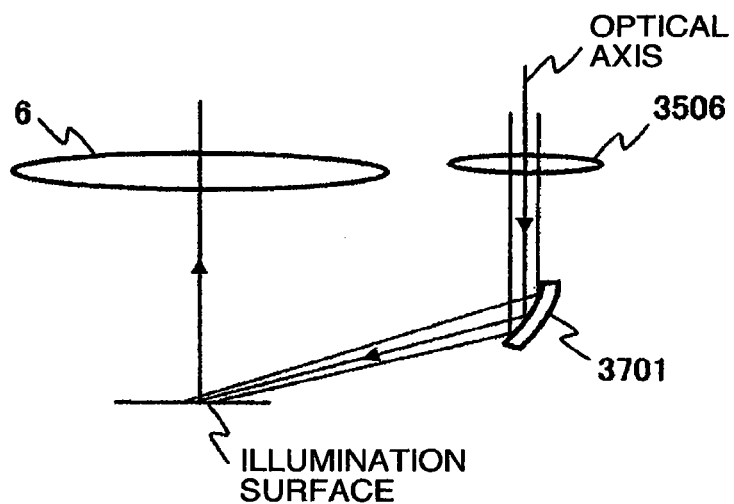
FIG. 17 shows an example of a total reflection mirror in the fourth embodiment of the invention.

FIG. 17 shows another example of the total reflecting mirror 3507. Whereas the example shown in FIG. 15 uses a sheet-like mirror for the total reflecting mirror 3507, the example shown in FIG. 17 uses a parabolic mirror 3701 for condensation. The advantage of the sheet-like mirror 3507 is that an economical optical component can be used and the cost of the apparatus can be reduced. On the hand, the advantage of the parabolic mirror 3701 is that it is effective when illumination of high luminance is necessary because the mirror can efficiently condense the rays of illumination light.

The fourth embodiment of the invention provides the effect that the polarization direction of each illumination irradiated to the wafer 1 can be controlled in addition to the effect analogous to that of the first embodiment.

The embodiment given above explains the method for conducting multi-direction illumination from eight directions to the visual field of the objective lens 6 but the illumination direction need not always be eight directions but may be a plurality of directions. The illumination direction of the rays of illumination light from the eight directions can be selected by shading them by a shutter, not shown in the drawing.

Fifth Embodiment

The fifth embodiment of the invention will be explained with reference to FIG. 18. In the fifth embodiment, the construction of a multi-region detecting unit is different from the multi-region detecting unit 7 in the first embodiment. The rest of the constructions are equivalent to those of the first embodiment.

Figure 18A:
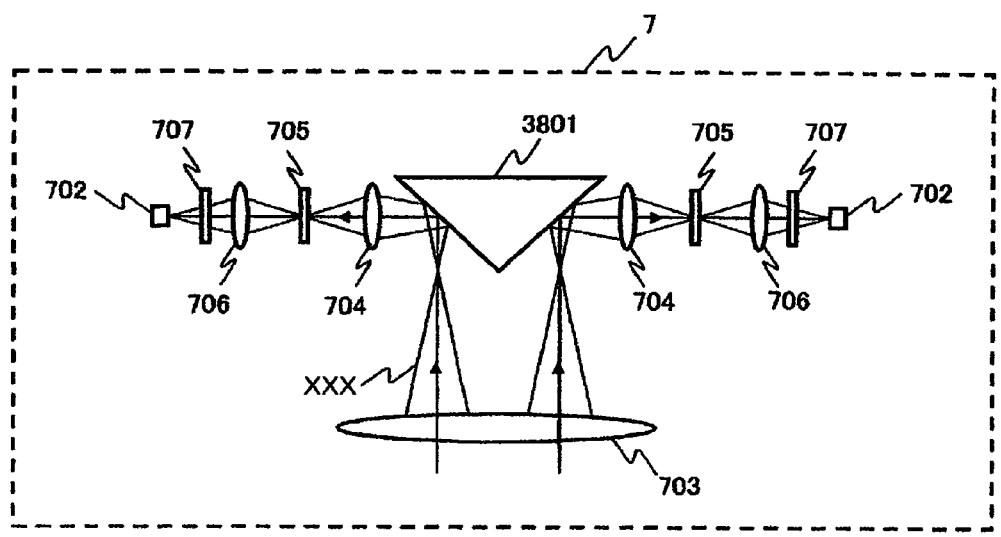
FIGS. 18A and 18B are detailed explanatory views of a multi-region detecting unit in the fifth embodiment of the invention.
Figure 18B:
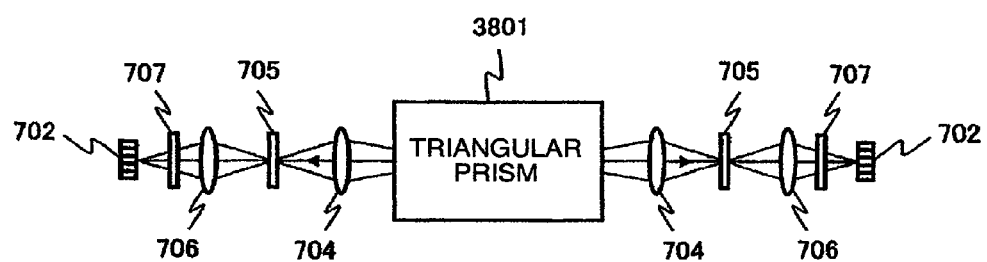

FIG. 18A shows the side surface of the multi-region detecting unit 7 in the fifth embodiment and FIG. 1B shows its upper surface. The multi-region detecting unit shown in FIG. 5 executes detection by dividing a plurality of illumination regions of the wafer 1 by the beam splitter 702 into transmission light and reflected light but the embodiment shown in FIG. 18 conducts detection by reflecting illumination light into two directions by a triangular prism 3801.

The fifth embodiment of the invention provides the effect that aberration due to detection of transmission light need not be made because reflected light of the triangular prism 3801 is detected, and the construction of the apparatus can be made economical in addition to the effect analogous to the first embodiment.

Sixth Embodiment

Next, the sixth embodiment of the invention will be explained with reference to FIG. 19. In this embodiment, a light power evaluating unit 3901 is added to the first embodiment (ADC unit 9 is omitted) and the rest of the constructions are analogous to those of the first embodiment.

Figure 19:
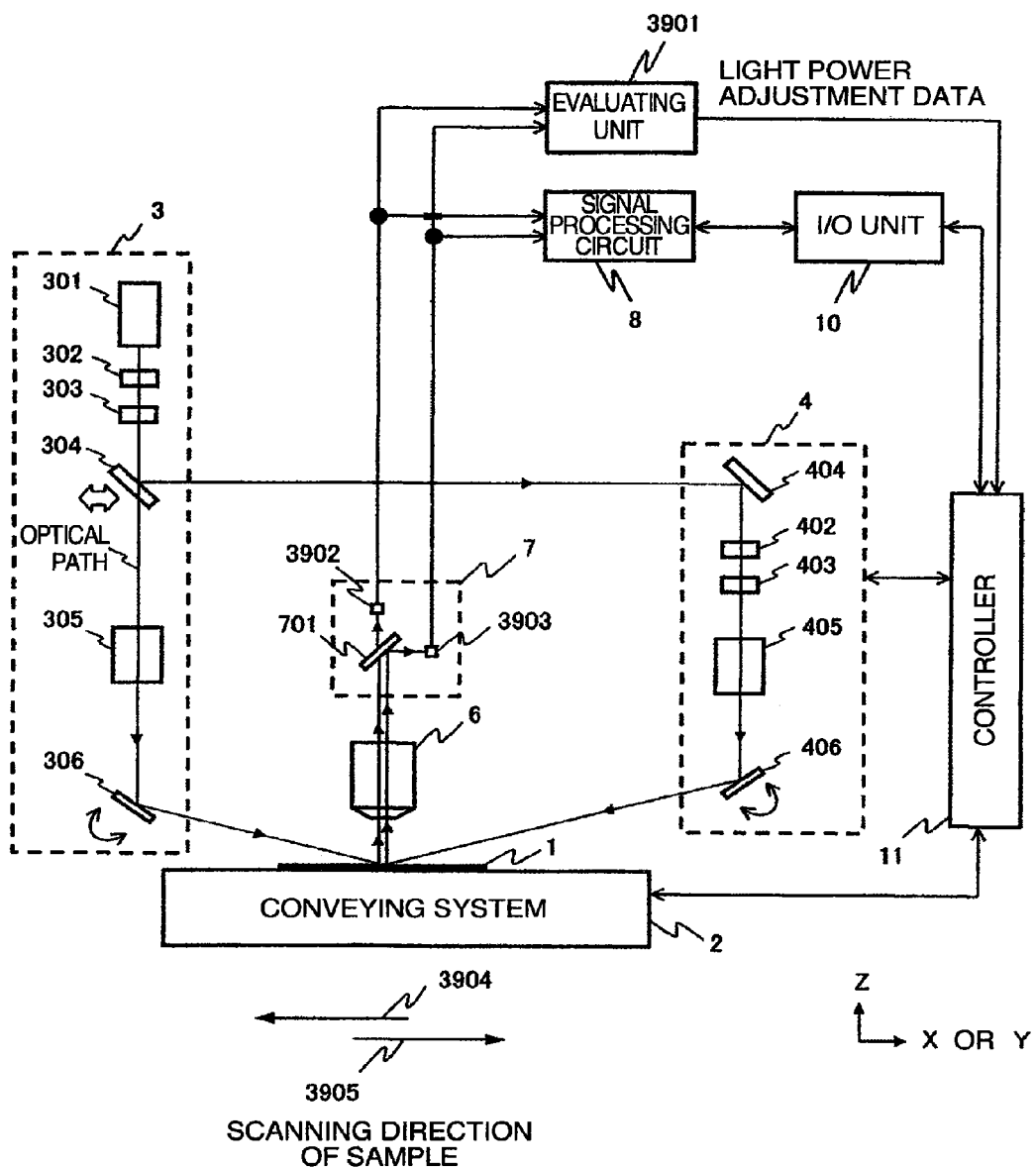
FIG. 19 is an overall schematic structural view in the sixth embodiment of the invention.

In FIG. 19, a detector 3902 and a detector 3903 are the same detector as the detector 702 shown in the first embodiment. The sixth embodiment of the invention represents the example where one of the two detectors 3902 and 3903 is used as a detector for measuring scattered light power from the wafer 1 while the other is used for detecting defects.

The operation of the sixth embodiment will be explained. In FIG. 19, the construction in which illumination light is irradiated to the wafer 1, the detector 3902 or 3903 detects the signal and the signal processing unit 8 detects the defect is the same as in the first construction. In the sixth embodiment of the invention, the construction in which illumination light power of the illumination region corresponding to the detector that makes detection in a later stage on the basis of detection light power of the detector making detection in an early stage when the wafer 1 is scanned by the conveying system 2 is added.

In FIG. 19, the detector 3902 makes detection of the same position of the wafer 1 during scanning in the scanning direction 3904 at an earlier timing than the detector 3903, and the detector 3903 conducts detection at an earlier stage in the scanning direction 3905 than the detector 3902. At this time, the region detected by the detector 3902 is illuminated by the illuminating unit 3 and the region detected by the detector 3903 is illuminated by the illuminating unit 4.

First, in the scanning direction 3904, the signal detected by the detector 3902 is sent to the light power evaluating unit 3901, which measures scattered light power from the wafer 1. When the signal gets into saturation in this instance, a signal representing that light power is excessive is outputted from the controller 11 to the light power polarization adjusting unit 402 to lower light power of the light power polarization adjusting unit 402. When the signal detected by the detector 3902 is small, a signal for increasing light power outputted from the controller 11 to the light power polarization adjusting unit 402. In consequence, illumination light power of the illuminating unit is adjusted to an optimal value and the signal quantity detected by the detector 3903 is optimized.

In the case of the scanning direction 3905, on the other hand, the light power evaluating circuit 3901 measures scattered light power from the wafer 1 on the basis of the signals detected by the detector 3903 and the light power polarization adjusting unit 302 adjusts light power and optimizes irradiation light power of the illuminating unit 3.

Because illumination light power to the wafer 1 can be adjusted on the real time basis by the operation described above, scattered light power incident to the detector 3902 or 3903 can be adjusted on the real time basis. Therefore, an optimal detection signal can be always detected within the dynamic ranges of the detectors 3902 and 3903 and various circuit patterns of the wafer 1 can be inspected with high sensitivity.

The sixth embodiment of the invention provides the effect that the dynamic range of the fine defect detector can be enlarged and various kinds of fine defects can be detected in addition to the effects analogous to those of the first embodiment.

The embodiment described above explains an example of adjustment of illumination light power. However, detection light power may be adjusted by interposing ND filters between the beam splitter 701 and the detector 3902 and between the beam splitter 701 and the detector 3903 or the gain of the analog signals of the detector 3902 or the detector 3903 may be adjusted. The method that adjusts the gain of the detector provides the advantage that the operation speed can be increased.

Seventh Embodiment

Figure 20:
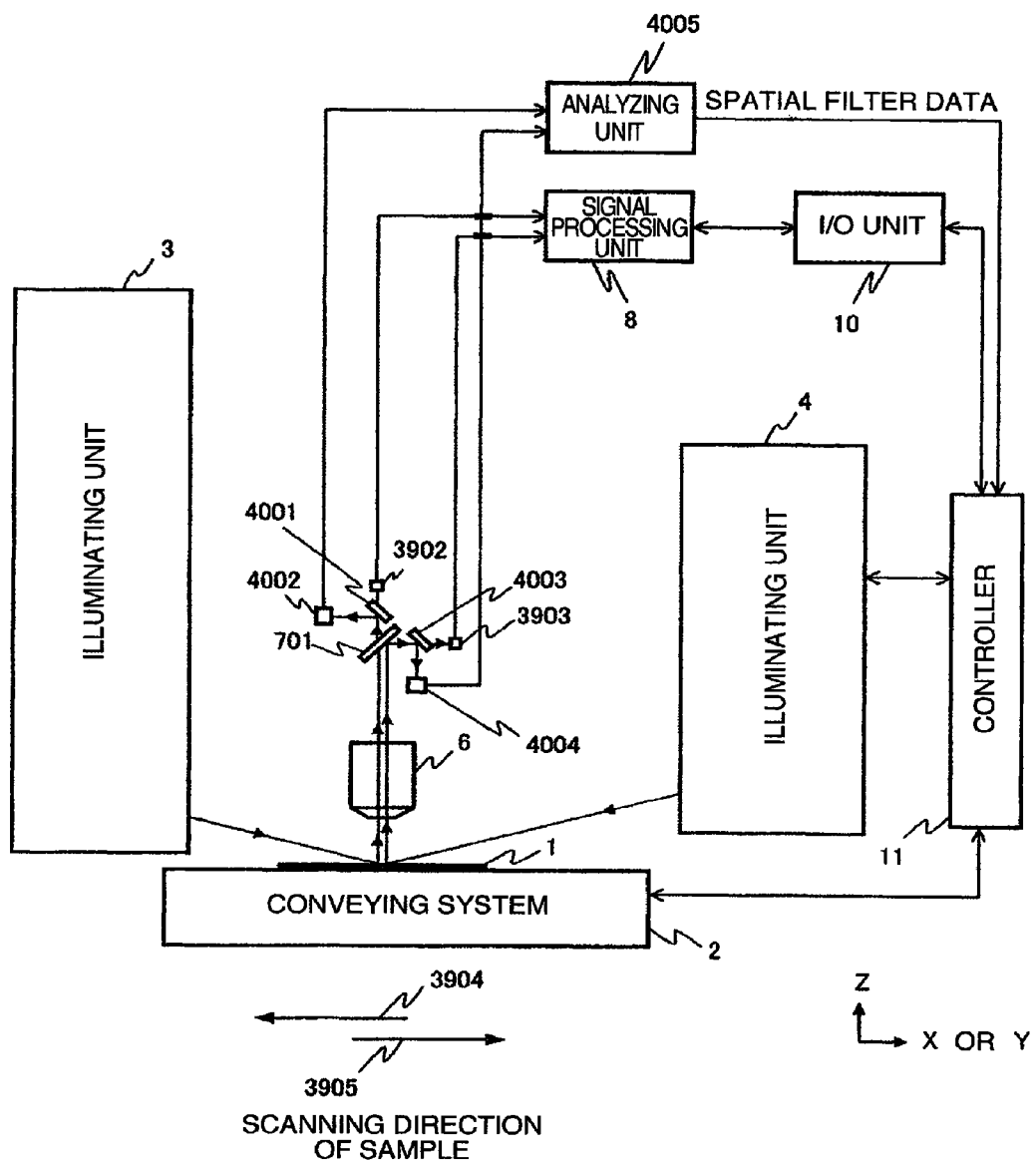
FIG. 20 is an overall schematic structural view in the seventh embodiment of the invention.

Next, the seventh embodiment of the invention will be explained with reference to FIG. 20. The seventh embodiment is constituted by adding beam splitters 4002 and 4003, Fourier transform image observing units 4002 and 4005 and a Fourier transform image analyzing unit 4005 to the first embodiment of the invention (ADC unit 9 is omitted). In the seventh embodiment, one of the optical paths branched by the beam splitter 701 images the Fourier transform image and decides a spatial filter and the other optical path conducts defect detection. The detectors 3902 and 3903 are of the same type as the detector 702 in the same way as the second embodiment. The rest of the constructions are the same as those of the first embodiment.

The operation of the seventh embodiment will be explained. In FIG. 20, illumination light is irradiated onto the wafer 1, the detector 3902 or 3903 detects the signal and the signal processing unit 8 detects the defect in the same way as in the first embodiment. The relation of the scanning direction, the timing of the signals detected by the detectors 3902 and 3903 and the illuminating units 3 and 4 is the same as that of the second embodiment.

Scattered light from the circuit pattern on the wafer 1 illuminated by the illuminating unit 3 or 4 passes through the objective lens 6 and is branched by the beam splitter 701 into the optical paths explained with reference to FIG. 5. The rays of illumination light branched by the beam splitter 701 towards the detector 3902 is branched by a beam splitter 4001. Reflected rays of light pass through the Fourier transform image observing unit 4002 and a Fourier transform image is imaged.

On the other hand, transmitted light of the beam splitter 4001 is detected as the image of the wafer 1 by the detector 3902. Here, the Fourier transform image observing unit 4002 is constituted by relay lenses and a TV camera that are not shown in the drawing. The rays of light branched by the beam splitter 701 towards the detector 3903 are subjected to the image formation by the Fourier transform image observing unit 4003 and the detector 3903 in the same way as the rays of light branched towards the detector 3902.

Next, the signals acquired from the Fourier transform image observing units 4002 and 4004 are sent to the Fourier transform image analyzing unit 4005. Here, the Fourier transform image analyzing unit 4005 has the functions of analyzing the Fourier transform image taken, recognizing the Fourier transform pattern and calculating data having a suitable spatial filter form. The data calculated by the Fourier transform image analyzing unit 4005 are position information to be shaded by the spatial filter.

The data calculated by the Fourier transform image analyzing unit 4005 are sent to the controller 11, can control the spatial filter 705 (not shown in FIG. 20) and can also change the shape of the spatial filter 705 on the real time basis.

The spatial filter 705 must be removed from optical paths that are not used for the defect detection.

Owing to the operations described above, scattered light from the wafer 1 can be optically erased on the real time basis and various kinds of circuit patterns of the wafer 1 can be inspected with high sensitivity.

In other words, the seventh embodiment of the invention provides the effects that scattered light from the wafer 1 can be optically erased on the real time basis and various kinds of circuit patterns of the wafer 1 can be inspected with high sensitivity in addition to the effects analogous to those of the first embodiment.

Eighth Embodiment

Next, the eighth embodiment of the invention will be explained with reference to FIGS. 21 to 25. The eighth embodiment relates to a defect inspection apparatus formed by adding a construction for inspecting a bevel portion of the wafer 1 to the defect inspection apparatus of each of the first to seventh embodiments. Here, the term "bevel portion" represents an end face portion of the wafer 1 shown in the sectional view of FIG. 22 and falls within the range of about 3 mm from the edge of the wafer 1.

Figure 21:
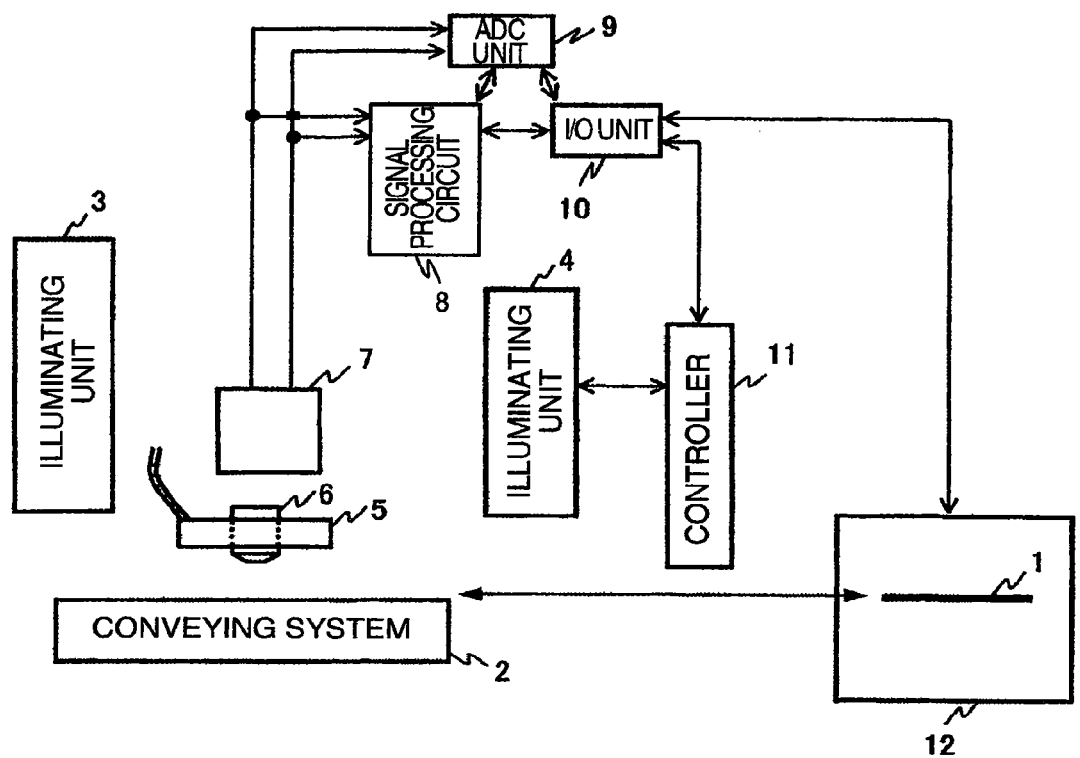
FIG. 21 is an overall schematic structural view in the eighth embodiment of the invention.

As shown in FIG. 21, the eighth embodiment includes a bevel inspecting unit 12 in addition to the embodiment shown in FIG. 1 and the rest of the constructions are the same as those of FIG. 1.

FIG. 23 shows the detail of the bevel inspecting unit 12. In the eighth embodiment, the case where the bevel portion is inspected by using a mechanism accessorial to the apparatus, for detecting a reference position in the rotating direction of the wafer 1, will be explained.

Figure 23A:
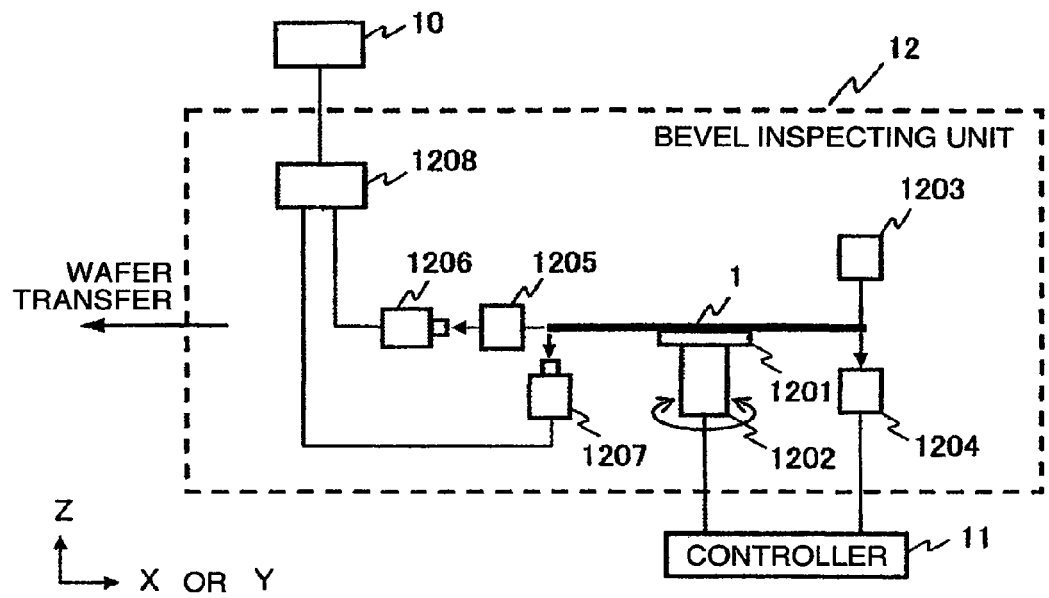
FIGS. 23A and 23B are explanatory views useful for explaining the detail of a bevel inspecting unit.
Figure 23B:
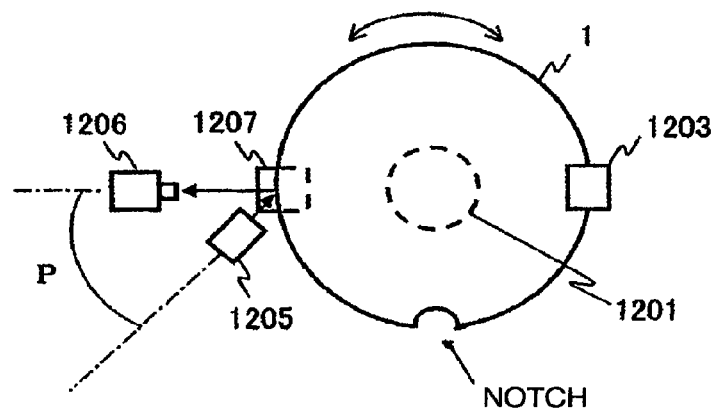

FIG. 23A shows the side surface of the bevel inspecting unit 12 and FIG. 23B shows its top surface. The bevel inspecting unit 12 includes a wafer chuck 1201, a rotary motor 1202, a sheet-like beam emitting unit 1203, a sheet-like beam receiving unit 1204, illumination light sources 1205, a TV camera 1206 and 1207, a data storing unit 1208 and relay lenses and mirrors both of which are not shown in the drawing.

Figure 22:
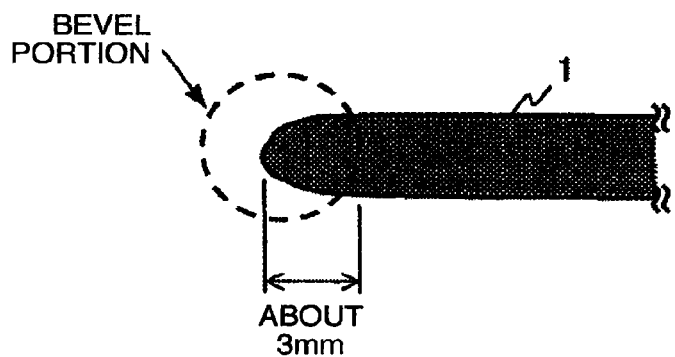
FIG. 22 is an explanatory view useful for explaining a bevel portion of a wafer.

The operation of the eighth embodiment will be explained. In FIGS. 21 to 23, the wafer 1 is taken out from a wafer cassette by a robot arm, not shown, and is fixed by vacuum adsorption on the wafer chuck 1201. Next, the sheet-like beam emitting unit 1203 emits a sheet-like beam.

Here, the sheet-like beam is a beam that is elongated in a direction parallel to the radial direction of the wafer 1 and the size of the beam and its position are set in such a fashion that the edge of the wafer 1 transversely crosses the sheet-like beam. The sheet-like beam emitted from the emitting unit 1203 is received by the sheet-like receiving unit 1204. The wafer 1 is rotated round the Z axis as its center by the rotary motor 1202 disposed on the wafer chuck 1201.

A hollow cut called "notch" is formed in the wafer 1 as the reference of the rotating direction. Therefore, the shading ratio of the sheet-like beam decreases at the notch portion when the wafer 1 is rotated whereas the beam reception quantity by the sheet-like beam receiving unit 1204 increases at the notch portion.

Figure 24:
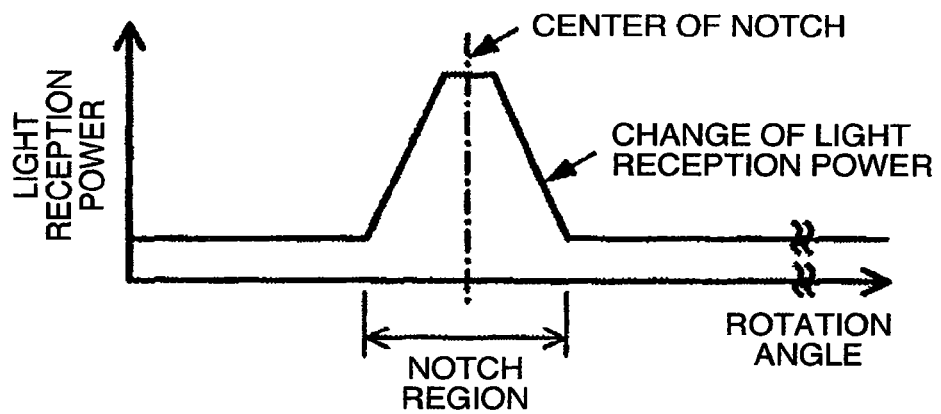
FIG. 24 is a graph useful for explaining the change of a light reception quantity of a sheet-like beam receiving unit.

FIG. 24 shows an example of the change of the beam reception quantity at this time. In FIG. 24, the abscissa represents the rotating angle moved by the rotary motor 1202 and the ordinate represents the beam reception quantity of the sheet-like beam receiving unit 1204. As described above, the transmission factor increases at the notch portion when the wafer 1 is rotated and the beam reception quantity increases. The waveform of the increase of the beam reception quantity changes depending on the shape of the notch but is generally trapezoidal or triangular. After this waveform data is acquired, the portion at which the beam reception quantity increases is recognized as the region of the notch and the center of this notch region is recognized as the center of the notch. In this way, the position of the notch as the reference of the rotating direction of the wafer 1 can be detected.

The eighth embodiment of the invention conducts detection of the bevel portion simultaneously with the detecting operation of the rotation reference position described above. After the wafer 1 is fixed as described above, the beam is emitted from the illumination light source 1205 and the bevel portion of the wafer 1 is illuminated from the direction P with respect to the center axis of the imaging region of the TV camera 1206. At this time, illumination light may be either white light or a laser beam. When any defect exists, strong scattered light occurs in the bevel portion illuminated by the illumination light source 1205 and is detected by the TV camera 1206.

On the other hand, scattered light is weak in the normal portion at which no defect exists and the TV camera 1206 detects nothing. The rays of light detected by the TV camera 1206 are sent to the data storing unit 1208 and scattered light power from the bevel portion is calculated.

Figure 25:
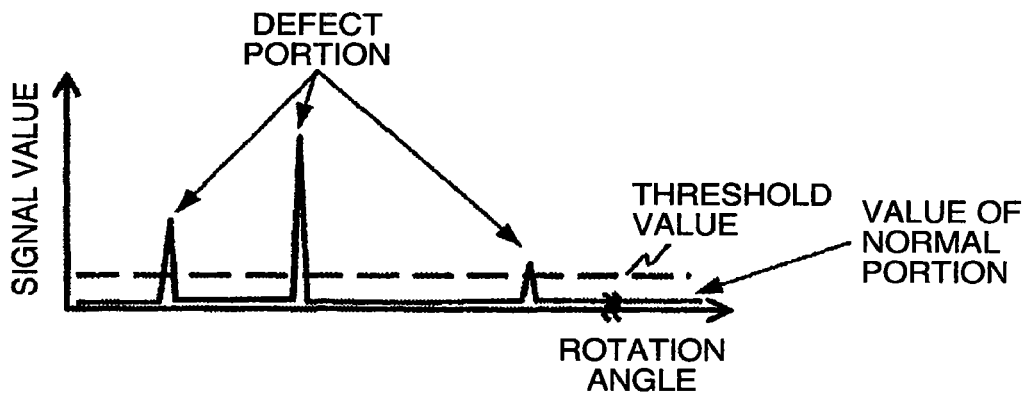
FIG. 25 is a graph useful for explaining the signal change of a TV camera for bevel inspection.

FIG. 25 shows an example of the signal change of the bevel portion. In FIG. 25, the abscissa represents the rotating angle moved by the rotary motor 1202 and the ordinate represents the signal value of the TV camera 1206. As shown in FIG. 25, the signal value becomes small at the normal portion and large at the defect portion. A pre-determined threshold value is set to this waveform and signals exceeding the threshold value are judged as being defect portions. The inspection of the bevel portion becomes thus possible.

Information of the defect detected is transmitted to the input/output unit 10 and is displayed on the display. The defect information is the defect position and the image of the TV camera 1206, for example. The advantage brought forth by outputting the image of the defect portion is that the defect portion becomes recognizable more easily.

As for the regions that cannot be imaged by the TV camera 1206, on the other hand, a TV camera 1207 may be added for imaging so as to detect the defect. The operation of the TV camera 1207 is the same as that of the TV camera 1206.

After sensing of the rotation reference position and the inspection of the bevel are completed, the wafer 1 is transferred to the conveying system 2 by the robot arm, not shown, and the wafer surface is inspected by any of the inspection apparatuses of the first to seventh embodiments.

Having the construction described above, the eighth embodiment of the invention can inspect highly precisely the surface of the wafer 1 in the same way as in the first to seventh embodiments and can also evaluate with high sensitivity the bevel portion of the wafer 1.

Incidentally, it would be obvious to those skilled in the art that the embodiments described above are mutually applicable.

The invention can be applied not only to the inspection of semiconductor wafers but also to the inspection of thin film substrates, photo masks, PDP, and so forth.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus which inspects a defect of a sample, comprising: an illumination system which forms a first illumination area on a surface of said sample and a second illumination area of said surface; a detection system which has a first field of view for said first illumination area and a second field of view for said second illumination area though an objective lens, and which includes a first detector corresponding to said first field of view and a second detector corresponding to said second field of view, said first detector being configured to output a first scattered signal and said second detector being configured to output a second scattered signal; and a processing system which processes at least one of said first scattered signal and said second signal, wherein said processing system includes a first gray level changing unit which changes a first gray level of said first scattered signal, and a second gray level changing unit which changes a second gray level of said second scattered signal; and a first normalizing filter for said first scattered signal, and a second normalizing filter for said second scattered signal.

2. The inspection apparatus according to claim 1, wherein said processing system integrates said first scattered signal with said second scattered signal.

3. The inspection apparatus according to claim 2, wherein said processing system acquires a normalized signal using said first scattered signal and said second signal.

4. The inspection apparatus according to claim 3, wherein said processing system includes a delay memory, and is configured to adjust a position associated with said normalized signal using a delayed signal from said delay memory.

5. The inspection apparatus according to claim 4, wherein said processing system detects a defect using a position adjusted signal determined by said processing system.

6. The inspection apparatus according to claim 1, wherein said processing system processes said first scattered signal and said second scattered signal individually.

7. The inspection apparatus according to claim 6, wherein said processing system includes a first delay memory for said first scattered signal, and a second delay memory for said second scattered signal.

8. The inspection apparatus according to claim 1, wherein said illumination system illuminates said sample with light from a plurality of directions.

9. The inspection apparatus according to claim 8, wherein said illumination system changes polarization directions of said light from a plurality of directions.

10. The inspection apparatus according to claim 9, wherein said polarization directions are S polarization and P polarization.

11. The inspection apparatus according to claim 9, wherein said illumination system includes a parabolic mirror.

12. The inspection apparatus according to claim 9, wherein said detection system includes a polarization detecting element.

13. The inspection apparatus according to claim 8, wherein said illumination system changes wavelengths of said light from among the plurality of directions.

14. The inspection apparatus according to claim 8, wherein said illumination system illuminates said sample using a fiber system.

15. The inspection apparatus according to claim 14, wherein said fiber system changes lengths of optical paths through which said light from the plurality of directions pass.

* * * * *